US006552170B1

(12) United States Patent
Thompson et al.

(10) Patent No.: US 6,552,170 B1
(45) Date of Patent: Apr. 22, 2003

(54) PEGYLATION REAGENTS AND COMPOUNDS FORMED THEREWITH

(75) Inventors: Robert C. Thompson, Boulder, CO (US); Michael T. Brewer, Boulder, CO (US); Tadahiko Kohno, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 08/259,413

(22) Filed: Jun. 14, 1994

Related U.S. Application Data

(63) Continuation-in-part of application No. 07/850,675, filed on Mar. 13, 1992, now abandoned, which is a continuation-in-part of application No. 07/669,862, filed on Mar. 15, 1991, now abandoned, which is a continuation-in-part of application No. 07/555,274, filed on Jul. 19, 1990, now abandoned, and a continuation-in-part of application No. 07/506,522, filed on Apr. 6, 1990, now Pat. No. 5,075,222.

(51) Int. Cl.[7] ............................. C07K 1/00; C07K 1/06; C07K 1/10; A61K 38/00
(52) U.S. Cl. ..................... 530/351; 435/177; 435/150; 435/181; 514/2; 514/12; 514/13; 514/14; 514/54; 525/50; 525/54.1; 525/54.11; 525/535; 424/94.3; 530/350; 530/357; 530/388.2; 530/323; 530/388.23; 530/388.85
(58) Field of Search ..................... 435/188; 514/2, 514/12, 13, 14; 525/50, 54.1, 54.11, 535; 530/357, 404, 351, 388.2, 388.23, 388.85

(56) References Cited

U.S. PATENT DOCUMENTS

| 4,179,337 A | 12/1979 | Davis et al. |
| 4,289,690 A | 9/1981 | Pestka et al. |

(List continued on next page.)

FOREIGN PATENT DOCUMENTS

| CA | 2003743 | 5/1990 |
| CA | 2039458 A1 | 10/1991 |
| DE | 39 10 323 A1 | 10/1989 |
| EP | 0 040 506 | 11/1981 |
| EP | 0 092 918 A2 | 11/1983 |
| EP | 0 094 844 A2 | 11/1983 |
| EP | 0 154 316 A2 | 9/1985 |
| EP | 0 169 112 B1 | 1/1986 |
| EP | 0 225 579 A3 | 6/1987 |
| EP | 0 247 860 A2 | 12/1987 |
| EP | 0 259 863 A2 | 3/1988 |
| EP | 0 308 378 B1 | 3/1989 |
| EP | 0 308 378 A2 | 3/1989 |
| EP | 0 154 316 B1 | 9/1989 |
| EP | 0 334 165 A2 | 9/1989 |
| EP | 0 343 684 B1 | 11/1989 |
| EP | 0 372 752 A2 | 6/1990 |
| EP | 0 386 289 A1 | 9/1990 |
| EP | 0 393 438 A2 | 10/1990 |
| EP | 0 395 853 A1 | 11/1990 |
| EP | 0 398 327 A1 | 11/1990 |
| EP | 0 412 486 A1 | 2/1991 |
| EP | 0 417 563 A2 | 3/1991 |
| EP | 0 418 014 A1 | 3/1991 |
| EP | 0 422 339 A1 | 4/1991 |
| EP | 0 433 900 A1 | 6/1991 |
| EP | 0 512 528 A2 | 11/1992 |
| EP | 0 526 905 A2 | 2/1993 |
| EP | 0 622 394 | 11/1994 |
| GB | 2 218 101 A | 11/1989 |
| GB | 2 246 569 A | 2/1992 |
| IL | 90339 | 5/1989 |
| JP | 62-185029 A | 8/1987 |
| JP | 2040399 A | 2/1990 |
| WO | WO 87/00056 A1 | 1/1987 |
| WO | WO 88/00837 A2 | 2/1988 |
| WO | WO 89/01946 A1 | 3/1989 |
| WO | WO 89/05145 A1 | 6/1989 |
| WO | WO 89/06546 A1 | 7/1989 |
| WO | WO 89/09220 A1 | 10/1989 |
| WO | WO 90/04413 A1 | 5/1990 |
| WO | WO 90/04650 A1 | 5/1990 |
| WO | WO 90/05755 A1 | 5/1990 |
| WO | WO 90/12874 A2 | 11/1990 |
| WO | WO 90/13575 A1 | 11/1990 |
| WO | WO 91/03553 A1 | 3/1991 |
| WO | WO 91/05047 A1 | 4/1991 |
| WO | WO 91/07190 A1 | 5/1991 |
| WO | WO 91/16437 A1 | 10/1991 |
| WO | WO 91/17184 A1 | 11/1991 |
| WO | WO 91/17249 A1 | 11/1991 |
| WO | WO 92/01002 A1 | 1/1992 |
| WO | WO 92/01472 A1 | 2/1992 |
| WO | WO 92/01474 A1 | 2/1992 |
| WO | WO 92/04384 A1 | 3/1992 |
| WO | WO 92/07076 A1 | 4/1992 |
| WO | WO 92/12724 A1 | 8/1992 |
| WO | WO 92/13095 A1 | 8/1992 |
| WO | WO 92/15682 A1 | 9/1992 |
| WO | WO 92/16221 A1 | 10/1992 |
| WO | WO 92/16555 A1 | 10/1992 |
| WO | WO 93/01498 | 1/1993 |
| WO | WO 93/07863 A1 | 4/1993 |

(List continued on next page.)

OTHER PUBLICATIONS

US 5,843,791, 12/1998, Hauptmann et al. (withdrawn).
Derwent Computer Abstract 92–348933/42 ; WO9216221 Armes et al, Oct. 1992.*
Derwent Computer Abstract 92–284678/34 ; WO9213095 Carmichael et al, Aug. 1992.*

(List continued on next page.)

Primary Examiner—Herbert J. Lilling
(74) Attorney, Agent, or Firm—Timothy J. Gaul; Ron K. Levy; Steven M. Odre

(57) ABSTRACT

Compounds are disclosed having the general formula $R_1$-X-$R_2$, wherein $R_1$ and $R_2$ are biologically active groups, at least one of which is polypeptidic. X is a non-peptidic polymeric group. $R_1$ and $R_2$ may be the same or different. Preferred $R_1$ and $R_2$ groups are TNF inhibitors.

15 Claims, No Drawings

U.S. PATENT DOCUMENTS

| | | | |
|---|---|---|---|
| 4,522,750 A | | 6/1985 | Ades et al. |
| 4,560,649 A | | 12/1985 | Saxena et al. |
| 4,578,335 A | | 3/1986 | Urdal et al. |
| 4,609,546 A | | 9/1986 | Hiratani |
| 4,670,417 A | | 6/1987 | Iwasaki et al. |
| 4,670,563 A | | 6/1987 | Gros et al. |
| 4,675,285 A | | 6/1987 | Clark et al. |
| 4,677,027 A | | 6/1987 | Porath et al. |
| 4,696,980 A | | 9/1987 | Porath et al. |
| 4,760,067 A | * | 7/1988 | Firestone ................... 514/522 |
| 4,766,106 A | | 8/1988 | Katre et al. |
| 4,789,658 A | | 12/1988 | Yoshimoto et al. |
| 4,791,192 A | | 12/1988 | Nakagawa et al. |
| 4,847,325 A | | 7/1989 | Shadle et al. |
| 4,902,502 A | | 2/1990 | Nitecki et al. |
| 4,904,584 A | | 2/1990 | Shaw et al. |
| 4,917,888 A | | 4/1990 | Katre et al. |
| 4,931,544 A | | 6/1990 | Katre et al. |
| 4,935,233 A | | 6/1990 | Bell et al. |
| 4,959,314 A | | 9/1990 | Mark et al. |
| 4,966,888 A | | 10/1990 | Saxena et al. |
| 5,075,222 A | * | 12/1991 | Hannum et al. ........... 435/69.1 |
| 5,089,261 A | | 2/1992 | Nitecki et al. |
| 5,093,475 A | | 3/1992 | Carroll et al. |
| 5,116,964 A | | 5/1992 | Capon et al. |
| 5,122,614 A | | 6/1992 | Zalipsky |
| 5,136,021 A | | 8/1992 | Dembinski et al. |
| 5,153,265 A | | 10/1992 | Shadle et al. |
| 5,162,430 A | | 11/1992 | Rhee et al. |
| 5,166,322 A | * | 11/1992 | Shaw et al. ................. 530/351 |
| 5,171,264 A | | 12/1992 | Merrill |
| 5,211,945 A | | 5/1993 | Wallach et al. |
| 5,214,131 A | | 5/1993 | Sano et al. |
| 5,252,714 A | | 10/1993 | Harris et al. |
| 5,344,915 A | | 9/1994 | LeMaire et al. |
| 5,359,032 A | | 10/1994 | Dayer et al. |
| 5,359,037 A | | 10/1994 | Wallach et al. |
| 5,382,657 A | | 1/1995 | Karasiewicz et al. |
| 5,395,760 A | | 3/1995 | Smith et al. |
| 5,446,090 A | * | 8/1995 | Harris et al. ................. 530/351 |
| 5,453,490 A | | 9/1995 | Hageman et al. |
| 5,478,925 A | | 12/1995 | Wallach et al. |
| 5,512,544 A | | 4/1996 | Wallach et al. |
| 5,569,779 A | * | 10/1996 | Sabahi et al. ............... 560/190 |
| 5,605,690 A | | 2/1997 | Jacobs et al. |
| 5,610,279 A | | 3/1997 | Brockhaus et al. |
| 5,633,145 A | | 5/1997 | Feldmann et al. |
| 5,681,566 A | | 10/1997 | Stevenson |
| 5,695,953 A | | 12/1997 | Wallach et al. |
| 5,712,155 A | | 1/1998 | Smith et al. |
| 5,739,208 A | | 4/1998 | Harris |
| 5,747,639 A | | 5/1998 | Seely |
| 5,808,029 A | | 9/1998 | Brockhaus et al. |
| 5,811,261 A | | 9/1998 | Wallach et al. |
| 5,863,786 A | | 1/1999 | Feldmann et al. |
| 5,958,409 A | | 9/1999 | Turk et al. |

FOREIGN PATENT DOCUMENTS

| | | |
|---|---|---|
| WO | WO 93/21946 A1 | 11/1993 |
| WO | WO 94/01483 | 1/1994 |
| WO | WO 94/06457 A1 | 3/1994 |
| WO | WO 94/06476 A1 | 3/1994 |
| WO | WO 95/06058 | 3/1995 |
| WO | WO 95/13312 | 5/1995 |
| WO | WO 95/16706 A1 | 6/1995 |
| WO | WO 96/09323 A1 | 3/1996 |
| WO | WO 96/12022 A1 | 4/1996 |

OTHER PUBLICATIONS

Abuchowski et al., "Effect of Covalent Attachment of Polyethylene Glycol on Immunogenicity and Circulating Life of Bovine Liver Catalase", *Journal of Biological Chemistry*, 252(11):3582–3586 (1977).

Akerblom et al., "Preparation and Characterization of Conjugates of Monoclonal Antibodies and Staphyolococcal Enterotoxin A Using a New Hydrophilic Cross–Linker", *Bioconjugate Chem.*, 4:455–466 (1993).

Beutler and Cerami, "The Biology of Cachectin/TNF–A Primary Mediator of the Host Response", *Ann. Rev. Immunol.*, 7:625–655 (1989).

Bevilacqua et al., "Recombinant tumor necrosis factor induces procoagulant activity in cultured human vascular endothelium: Characterization and comparison with the actions of interleukin 1", *Proc. Natl. Acad. Sci. USA*, 83:4533–4537 (1986).

Bowie et al., "Deciphering the Message in Protein Sequences: Tolerance to Amino Acid Substitutions," *Science*, 247:1306–1310 (1990).

Brakebusch et al., "Diverse Functions of the Tumor Necrosis Factor Receptors: Structure–Activity Considerations", *Tumor Necrosis Factor: Molecular and Cellular Biology and Clinical Relevance*, pp. 40–51 (1993).

Brockhaus et al., "Identification of Two Types of Tumor Necrosis Factor Receptors of Human Cell Lines by Monoclonal Antibodies," *Proc. Natl. Acad. Sci. USA*, 87:3127–3131 (1990).

Chen et al., "Production of Multimeric Forms of CD4 Through a Sugar–based Cross–linking Strategy," *J. Biol. Chem.*, 266(27): 18237–18243 (1991).

Conforti et al., "PEG Superoxide Dismutase Derivatives: Anti–inflammatory Activity In Carrageenan Pleurisy in Rats", *Pharmacological Research Communications*, 19(4):287–294 (1987).

Creasey et al., "A High Molecular Weight Component of the Human Tumor Necrosis Factor Receptor is Associated with Cytotoxicity," *Proc. Natl. Acad. Sci. USA*, 84:3293–3297 (1987).

Davis et al., "Soluble, Nonantigenic Polyethylene Glycol–Bound Enzymes", *Biomedical Polymers: Polymeric Materials and Pharmaceuticals for Biomedical Use*, Goldberg et al. (Ed.). published by Academic Press (NY), pp. 441–451 (1980).

Dayer et al., "Purification and Characterization of Human Tumor Necrosis Factor Inhibitor," *Chemical Abstracts*, 113(38760n):454 (1990).

Delgado et al., "The Uses and Properties of PEG–Linked Proteins," *Critical Reviews in Therapeutic Drug Carrier Systems*, 9(3,4):249–304 (1992).

Dembic et al., "Two Human TNF Receptors Have Similar Extracellular, But Distinct Intracellular, Domain Sequences," *Cytokine*, 2(4):231–237 (1990).

Dohlsten et al., "Monoclonal Antibody–targeted Superantigens: A Different Class of Anti–tumor Agents", *Proc. Natl Acad. Sci. USA*, 88:9287–9291 (1991).

Eisenberg et al., "Primary structure and functional expression from complementary DNA of a human interleukin–1 receptor anatgonist", *Nature*, 343:341–346 (1990).

Engelmann et al., "A Tumor Necrosis Factor–Binding Protein Purified to Homogeneity from Human Urine Protects Cells from Tumor Necrosis Factor Toxicity," *J. Biol. Chem.*, 264(20):11974–11980 (1989).

Engelmann et al., "Two Tumor Necrosis Factor–Binding Proteins Purified From Human Urine," *J. Biol. Chem.*, 265(3):1531–1536 (1990).

Erez et al., "Narcotic Antagonistic Potency of Bivalent Ligands Which Contain—Naltrexamine Evidence for Bridging Between Proximal Recognition Sites," *J. Med. Chem.*, 25:847–849 (1982).

Glass et al., "4–Phenoxy–3,5–Dinitrobenzoylpolyethyleneglycol: Reversible Attachment of Cysteine–Containing Polypeptides to Polymers in Aqueous Solutions", *Biopolymers*, 18:383–392 (1979).

Goodson et al., "Site–Directed Pegylation of Recombinant Interleukin–2 At Its Glycosylation Site," *BioTechnology*, 8:343–346 (1990).

Gray et al., "Cloning of Human Tumor Necrosis Factor (TNF) Receptor cDNA and Expression of Recombinant soluble TNF–Binding Protein," *Proc. Natl. Acad. Sci. USA*, 87(19):7380–7384 (1990).

Hale et al., "Cytokines and Their Receptors: From Clonal to Clinical Investigation, Demonstration of In Vitro and In Vivo Efficacy of Two Biologically Active Human Soluble TNF Receptors Expressed in *E. Coli,*" *J. Cell.* Biochem., Suppl. 15F:113 (1991).

Hannum et al., "Interleukin–1 receptor antagonist activity of a human interleukin–1 inhibitor", *Nature*, 343:336–340 (1990).

Harris, Milton, "Laboratory Synthesis of Polyethylene Glycol Derivatives", *Rev. Macromol. Chem. Phys.*, 25(3):325–373 (1985).

Harris et al., "Synthesis and Chracterization of Poly(ethylene Glycol) Derivatives," *Journal of Polymer, Science: Polymer Chemistry Addition*, 22:341–352 (1984).

Heller et al., "Amplified Expression of Tumor Necrosis Factor Receptor in Cells Transfected with Epstein–Barr Virus Shuttle Vector cDNA Libraries," *J. Biol. Chem.*, 265(10):5708–5717 (1990).

Heller et al., "Complementary DNA Cloning of a Receptor for Tumor Necrosis Factor and Demonstration of a Shed Form of the Receptor," *Proc. Natl. Acad. Sci. USA*, 87:6151–6155 (1990).

Himmler et al., "Molecular Cloning & Expression of Human & Rat Tumor Necrosis Factor Receptor Chain (p60) and Its Soluble Derivative, Tumor Necrosis Factor–Binding Protein," *DNA and Cell Biology*, 9(10):705–715 (1990).

Hoes et al., "Optimization of Macromolecular Prodrugs of the Antitumor Antibiotic Adriamycin", *Journal of Controlled Release*, 2:205–213 (1985).

Jiang et al., "Defined Chemically Cross–Linked Oligomers of Human C–Reactive Protein: Characterization and Reactivity with the Complement System", *Immunology*, 74:725–731 (1991).

Johansson, Gote, "Studies on Aqueous Dextran–Poly(Ethylene Glycol) Two–Phase Systems Containing Charged Poly(Ethylene Glycol)", *Biochimica Et Biophysica Acta*, 222:381–389 (1970).

Katre et al., "Chemical modification of recombinant interleukin 2 by polyethlene glycol increases its potency in the murine Meth A sarcoma model", *Proc. Natl. Acad. Sci. USA*, 84:1487–1491 (1987).

Kogan et al., "The Synthesis of Substituted Methoxy–Poly–(Ethylene Glycol) Derivatives Suitable for Selective Protein Modification", *Synthetic Communications*, 22(16):2417–2424 (1992).

Kohno et al., "A Second Tumor Necrosis Factor Receptor Gene Product Can Shed a Naturally Occuring Tumor Necrosis Factor Inhibitor," *Proc. Natl. Acad. Sci. USA*, 87:8331–8335 (1990).

Kuroki et al., "Aryl Vinyl Sulfones as Thiol Protective Group", *Tetrahedron Letters*, 25(2):197–200 (1984).

Lantz et al., "Characterization In Vitro of a Human Tumor Necrosis Factor–Binding Protein," *J. Clin. Invest.*, 86(5):1396–1402 (1990).

Liao et al., "Characterization of a human inteleukin 1 inhibitor", *J. Immunol.*, 134(6):3882–3886 (1985).

Loetscher et al., "Molecular Cloning and Expression of the Human 55kd TNF Necrosis Factor Receptor," *Cell*, 61:351–359 (1990).

Loetscher et al., "Recombinant 55–kDa Tumor Necrosis Factor (TNF) Receptor," *J. Biol. Chem.* 266(27):18324–18329 (1991).

Marangonore et al., "Design and Characterization of Hirulogs: A Novel Class of Bivalent Peptide Inhibitors of Thrombin", *Biochemistry*, 29:7095–7101 (1990).

Murata et al., "Inhibitory Effect of a Synthetic Polypeptide, poly(Tyr–Ile–Gly–Ser–Arg), On The Metastatic Formation of Malignant Tumour Cells", *Int. J. Biol. Macromol.*, 11:97–99 (1989).

Nophar et al., "Soluble forms of tumor necrosis factor receptors (TNF–Rs). The cDNA for the type I TNF–R, cloned using amino acid sequence data of its soluble form, encodes both the cell surface and a soluble form of the receptor," *The EMBO J.*, 9(10):3269–3278 (1990).

Olsson et al., "Isolation and Characterization of a Tumor Necrosis Factor Binding Protein from Urine," *Eur. J. Haematology*, 42(3):270–275 (1989).

Peetre et al., "A Tumor Necrosis Factor Binding Protein is Present in Human Biological Fluids," *Eur. J. Haematology*, 41:414–419 (1988).

Peppel et al., "A Tumor Necrosis Factor (TNF) Receptor–IgG Heavy Chain Chimeric Protein as a Bivalent Antagonist of TNF Activity," *J. Exp. Med.*, 174:1483–1489 (1991).

Portoghese et al., "Opioid Agonist and Antagonist Bivalent Ligands. The Relationship Between Spacer Length and Selectivity at Multiple Opioid Receptors", *J. Med. Chem.*, 29:1855–1861 (1986).

Rhein et al., "Another Sepsis Drug Down—Immunex[1] TNF Receptor," Biotechnology *Newswatch*, p. 1, 3(Monday, Oct. 4, 1993).

Romani et al., "Synthesis of Unsymmetrical Peptides: Directed Disulfide Pairing with the Sulfenohydrazide Method", *Chemistry of Peptides and Proteins*, 2:29–34 (1984).

Rosenstreich et al., "A human urine–derived interleukin 1 inhibitor", *J. Exp. Med.*, 168:1767–1799 (1988).

Schall et al., "Molecular Cloning and Expression of a Receptor for Human Tumor Necrosis Factor," *Cell*, 61:361–370 (1990).

Seckinger et al., "A Human Inhibitor of Tumor Necrosis Factor Alpha," *J. Exp. Med.*, 167:1511–1516 (1988).

Seckinger et al., "Characterization of a Tumor Necrosis Factor (TNF–) Inhibitor: Evidence of Immunological Cross– Reactivity with the TNF Receptor," *Proc. Natl. Acad. Sci. USA*, 87:5188–5192 (1990).

Seckinger et al., "Purification and Biologic Characterization of a Specific Tumor Necrosis Factor Inhibitor," *J. Biol. Chem.*, 264(20):11966–11973 (1989).

Seely et al., "Manufacturing of Recombinant TNF Binding Protein Dumbell Using a 20K PEG BIS–Vinylsufone Linker," 209th Am. Chem. Soc. National Meeting, Anaheim, Cal., Apr. 2–6, 1995, Abstract No. 95: 239228.

Shimohigashi et al., "Dimeric Tetrapeptide Enkephalins Display Extraordinary Selectivity for the Opiate Receptor", *Nature,* 297:333–335 (1982).

Smith et al., "A Receptor for Tumor Necrosis Factor Defines an Unusual Family of Cellular and Viral Proteins," *Science,* 248:1019–1023 (1990).

Smith et al., "Species Specificity of Human and Murine Tumor Necrosis Factor," *J. Biol. Chem.,* 261(32):14871–14874 (1986).

Stauber et al., "Human Tumor Necrosis Factor–alpha Receptor," *J. Biol. Chem.,* 263(35):19098–19104 (1988).

Suzuki et al., "Physicochemical and Biological Properties of Poly(Ethylene Glycol)–Coupled Immunoglobulin G", *Biochimica Et Biophysica Acta.,* 788:248–255 (1984).

Van Zee et al., "Tumor Necrosis Factor Soluble Receptors Circulate During Experimental and Clinical Inflammation and Can Protect Against Excessive Tumor Necrosis Factor alpha In Vitro and In Vivo", *PNAS,* 89:4845–4849 (1992).

Weisman et al., "Soluble Human Complement Receptor Type I: In Vivo Inhibitor of Complement Suppressing Post–Ischemic Myocardial Inflammation and Necrosis", *Science,* 249:146–151 (1990).

Zalipsky, Samuel, "Synthesis of an End–Group Functionalized Polyethlene Glycol–Lipid Conjugate for Preparation of Polymer–Grafted Liposomes", *Bioconjugate Chem.,* 4:296–299 (1993).

Aggarwal, et al., "Characterization of Receptors for Human Tumour Necrosis Factor and Their Regulation by γ–Interferon", *Nature,* 318:665–667 (1985).

Anderson et at., "Quantative Filter Hybridisation," Nucleic Acid Hybridization: A Practical Approach, Hawes et al. (ed)., pp. 73–111 (1985).

Ashkenazi et al., "Protection Against Endotixic Shock by a Tumor Necrosis Factor Receptor Immunoadhesin", *PNAS* 88: 10535–10539 (1991).

Baglioni et al., "Binding of Human Tumor Necrosis Factor to High Affinity Receptors on HeLa and Lymphoblastoid Cells Sensitive to Growth Inhibition", *Journal of Biological Chemistry,* 260(25):13395–13397 (1985).

Baker et al., "Inhibition of EAE by TNF–Receptor Fusion Proteins", *J. Neuroimmunology,* 54(1–2):151 Abstract P16.01 (1992).

Bakouche et al., "Plasma Membrane–Associated Tumor Necrosis Factor, A Non–Integral Membrane Protein Possibly Bound to Its Own Receptor," *J. Immunol.* 140:1142–1147 (1988).

Banner et al., "Crystal Structure of the Soluble Human 55 KD TNF Receptor–Human TNFβ Complex: Implications for TNF Receptor Activation", *Cell,* 73:431–445 (1993).

Beutler et al., "Passive Immunization against Cachectin/Tumor Necrosis Factor Protects Mice form Lethal Effect of Endotoxin", *Science,* 229:869–871 (1985).

Binkert et al., "Cloning, Sequence Analysis and Expression of a cDNA Encoding a Novel Insulin–like Growth Factor Binding Protein (IGFBP–2)," *The EMBO J.* 8(9):2497–2502 (1989).

Bourdon et al., "Structure–function Relationships of Hirulog Peptide Interactions with Thrombin", *FEBS* 294:163–166 (1991).

Brennan et al., "Inhibitory Effect of the TNFα Antibodies on Synovial Cell Interleukin–1 Production in Rheumatoid Arthritis," Lancet, vol. 2 (8657), pp. 244–247 (1989).

Byrn et al., "Biological Properties of a CD4 Immunoadhesin," *Nature (London)* 344:667–670 (1990).

Capaldi et al., "Changes in Order of Migration of Polypeptides in Complex III and Cytochrome c̲ Oxidase under Different Conditions of SDS Polyacrylamide Gel Electrophoresis," *Biochem. & Biophys. Res Comm.* 74(2):425–433 (1977).

Carlino et al., *"Use of a Sensitive Receptor Binding Assay to Discriminate Between Full–Length and Truncated Human Recombinant TNF Proteins", J. Biol. Chem.* 262(3):958–961 (1987).

Carrieri et al., "Cytokines in the Pathogenesis of Multiple Sclerosis", *Acta Neurolgica,* 14(4–6):p. 333–341 (1992).

Chaudhary et al., "A recombinant immunotoxin consisting of two antibody variable domains fused to Pseudomonas exotoxin," *Nature,* 339:394–397 (1989).

Colletti et al., "The Production of Tumor Necrosis Factor Alpha and the Development of a Pulmonary Capillary Injury Following Hepatic Ischemia/Reperfusion," *Transplantation* 49(2):268–272 (1990).

Engelmann et al., "Antibodies to a Soluble Form of a Tumor Necrosis Factor (TNF) Receptor Have TNF–Like Activity", *Journal of Biological Chemistry,* 265(24):14497–14504 (1990).

Espevik et al., "Characterization of Binding and Biological Effects of Monoclonal Antibodies Against a Human Tumor Necrosis Factor Receptor", *Journal Exp. Med.,* 171:415–426 (1990).

Evans, Ronald M., "The Steroid and Thyroid Hormone Receptor Superfamily," *Science* 240:889–895 (1998).

Frohman et al., "Rapid production of full–length cDNAs from rare transcripts: Amplification using a single gene–specific oligonucleotide primer," *Proc. Natl. Acad. Sci. USA* 85:8998–9002 (1988).

Gatanaga et al., "Purfication and Characterization of an Inhibitor (Soluble Tumor Necrosis Factor Receptor) for Tumor Necrosis Factor and Lymphotoxin Obtained from the Serum Ultrafiltrates of Human Cancer Patients," *Proc. National Academy of Science USA* 87:8781–8784 (1990).

Goodwin et al., "Molecular Cloning and Expression of the Type 1 and Type 2 Murine Receptors for Tumor Necrosis Factor," *Molecular and Cell Biology* 11(6):3020–3026 (1991).

Grizzard et al.., "Affinity–Labeled Somatomedin–C Receptors and Binding Proteins From the Human Fetus", *Journal of Clinical Endocrinology and Metabolism,* 58(3): 535–543 (1984).

Hass et al., "Characterization of Specific High Affinity Receptors for Human Tumor Necrosis Factor on Mouse Fibroblasts," *J. Biol. Chem.* 260(22):12214–12218 (1985).

Hatakeyama et al., "Interleukin–2 Receptor β Chain Gene: Generation of Three Receptor Forms by Cloned Human α and β Chain cDNA's," *Science* 244:551–556 (1989).

Hauser et al., "Cytokine Accumulations in CSF of Multiple Sclerosis Patients: Frequent Detection of Interleukin–1 and Tumor Necrosis Factor but not Interleukin–6," *Neurology* 40:1735–1739 (1990).

Hofman et al., "Tumor Necrosis Factor Identified in Multiple Sclerosis Brain," *J. Exp. Med.* 170:607–612 (1989).

Hohmann et al., "Two Different Cell Types Have Different Major Receptors for Human Necrosis Factor (TNF alpha)," *Journal of Biol. Chem.* 264: 14927–14934 (1989).

Horner et al., "Aryl–vinlysulfone–reagentien Zum Schutz Und Nacheweis Von Thiolfunktionen," *Phosphorus and Sulfur* 15:1–8 (1983).

Israel et al., "Binding of Human TNF–alpha to High–Affinity Cell Surface Receptors: Effect of IFN," *Immunol. Lett.* 12:217–224 (1986).

Jenkins et al., "Tumour Necrosis Factor Causes an Increase in Axonal Transport of Protein and Demyelination in the Mouse Optic Nerve", *Journal of Neurological Sciences*, 108:99–104 (1992).

Kalli et al., "Mapping of the C3b–binding Site of CR 1 and Construction of a $(CR\ 1)_2$–$F(ab')_2$ Chimeric Complement Inhibitor," *J. Exp. Med.* 174:1451–1460 (1991).

Kasukabe et al., "Purification of a Novel Growth Inhibitory Factor for Partially Differentiated Myeloid Leukemic Cells," *Journal of Biol. Chem.* 263(11):5431–5435 (1988).

Knauf et al., "Relationship of Effective Molecular Size to Systemic Clearance in Rats of Recombinant Interleukin–2 Chemically Modified with Water–soluble Polymers", *The Journal of Biological Chemistry*, 263(29):15064–15070 (1988).

Kohgo et al., "Circulating transferrin receptor in human serum", *British Journal of Haematology*, 64:277–281 (1986).

Kull et al., "Cellular Receptor for $^{125}$I–Labeled Tumor Necrosis Factor: Specific Binding, Affinity Labeling, and Relationship to Sensitivity," *Proc. Natl. Acad. Sci. USA*, 82:5756–5760 (1985).

Le et al., "Tumor Necrosis Factor and Interleukin 1: Cytokines with Multiple Overlapping Biological Activities," *Lab Investigation* 56(3):234–248 (1987).

Lee et al., "Generation of cDNA Probes Directed by Amino Acid Sequence: Cloning of Urate Oxidase," *Science* 239:1288–1291 (1988).

Lehmann et al., "Demonstration of Membrane Receptors for Human Natural and Recombinant $^{125}$I–Labeled Tumor Necrosis Factor on HeLa Cell Clones and Their Role in Tumor Cell Sensitivity," *Eur. J. Biochem.* 158:1–5 (1986).

Leung et al., "Growth Hormone Receptor and Serum Binding Protein: Purification, Cloning and Expression," *Nature* 330:537–543 (1987).

Liao et al., "Identification of a Specific Interleukin 1 Inhibitor in the Urine of Febrile Patients," *J. Exp. Med.* 159:126–136 (1984).

Liblau et al., "Tumor Necrosis Factor–α and Disease Progression in Multiple Sclerosis," *New Engl. J. Med.* 326(4):272–273 (1992).

Lindvall et al., "Modulation of the Constitutive Gene Expression of the 55 KD Tumor Necrosis Factor Receptor in Hematopoietic Cells," *Biochem. & Biophys. Res. Comm.* 172(2)557–563 (1990).

March et al., "Cloning, Sequence and Expression of Two Distinct Human Interleukin–1 Complementary DNAs," *Nature* 315:641–647 (1985).

McFarland et al., "Therapeutic Approaches to Multiple Sclerosis", *J. Neurochem.,* 64(Suppl.):S73 (Abstract C) (1995).

Monastra et al., "Phosphatidylserine, a Putative Inhibitor of Tumor Necrosis Factor, Prevents Autoimmune Demyelination", *Neurology*, 43:153–163 (1993).

Neda, Hiroshi, "Analysis of the Tumor Necrosis Factor (TNF) Receptor of Various Tumor Cells,"*Sapporo Medical Journal*, 56(2):305–317 (1987). (Abstract in English, first page).

Nexo et al., "Lectin–Agarose Immobilization, a New Method for Detecting Soluble Membrane Receptor," *J. Biol. Chem.* 254(18):8740–8743 (1979).

Novick et al., "Soluble Cytokine Receptors are Present in Normal Human Urine," *J. Exp. Med.* 170:1409–1414 (1989).

Novick et al., "Soluble Cytokine Receptors are Present in Normal Human Urine," *The Physiological and Pathological Effects of Cytokines*, pp. 413–421 (1990).

Novick et al., "Purification of Soluble Cytokine Receptors from Normal Human Urine by Ligand–Affinity and Immunoaffinity Chromatography," *J. Chromatog.* 510:331–337 (1990).

Pennica et al., "Biochemical Properties of the 75–kDa Tumor Necrosis Factor Receptor", Journal of Biological Chemistry, 267(29):21172–21178 (1992).

Piguet et al., "Tumor Necrosis Factor/Cachectin Plays a Key Role in Bleomycin–Induced Pneumopathy and Fibrosis," *J. Exp. Med.* 170:655–663 (1989).

Powell et al., "The Role of Lymphotoxin and TNF in Demyelination Diseases of the CNS", *Tumor Necrosis Factors: The Molecules and Their Emerging Role in Medicine*, ed. by B. Beutler; Raven Press, New York, pp. 355–369, (1992).

Powell et al., "Lymphotoxin and tumor necrosis factor–alpha production by myelin basic protein–specific T cell clones correlates with encephalitogenicity", *International Immunology*, 2(6): 539–544, (1989).

Ruddle et al., "An Antibody to Lymphotoxin and Tumor Necrosis Factor Prevents Transfer of Experimental Allergic Encephalomyelitis," *J. Exp. Med.* 172:1193–1200 (1990).

Scheurich et al., "Qualification and Characterization of High–Affinity Membrane Receptors for Tumor Necrosis Factor on Human Leukemic Cell Lines," *Int. J. Cancer* 38(1):127–133 (1986).

Seckinger et al., "A Urine Inhibitor of Interleukin 1 Activity Affects Both Interleukin 1 α and 1 β But Not Tumor Necrosis Factor α," *J. Immunol.* 139(5):1541–1545 (1987).

Seckinger et al., "A Urine Inhibitor of Interleukin 1 Activity That Blocks Ligand Binding." *J Immunol.* 139(5):1546–1549 (1987).

Selmaj et al., "Anti–Tumor Necrosis Factor Therapy Abrogates Autoimmune Demyelination",*Annals of Neurology by Am. Neurol. Assoc.*, 30(5):694–700 (1991).

Selmaj et al, "Prevention of CHR–EAE with Soluble TNF Receptor P55", *J. Neuroimmunology*, 54(12):196, Abstract W15.05 (1994).

Selmaj et al, "Prevention of Chronic Relapsing Experimental Autoimmune Encephalomyelitis by Soluble Tumor Necrosis Factor Receptor I", *J. Neuroimmunology*, 56:135–141 (1995).

Selmaj et al., "Proliferation of Astrocytes In Vitro In Response to Cytokines: A Primary Role for Tumor Necrosis Factor," *J. Immunol.* 144(1):129–135 (1990).

Selmaj et al., "Tumor Necrosis Factor Mediates Myelin and Oligodendrocyte Damage In Vitro," *Annals of Neurology* 23(4):339–346 (1998).

Sharief et al., "Association Between Tumor Necrosis Factor–Alpha and Disease Progression in Patients With Multiple Sclerosis," *New England J of Med.* 325(7):467–472 (1991).

Smith, Craig, "cDNA Expression: Cloning of the Receptor for Human Tumor Necrosis Factor." Presentation Programme, 29th Midwinter Conference of Immunologists (Jan. 27–30, 1990).

Smith, Craig, "cDNA Expression: Cloning of the Receptor for Human Tumor Necrosis Factor." Presentation at the 29th Midwinter Conference of Immunologists (Jan. 27–30, 1990).

Smith et al., "A Receptor for Tumor Necrosis Factor Defines an Unusual Family of Cellular and Viral Proteins," Genbank database excerpt released after publication (May 1990) (original Smith article on previous 1449).

Socher et al., "Antibodies against amino acids 1–15 of tumor necrosis factor block its binding cell–surface receptor," *Proc. Natl. Acad. Sci. USA* 84:8829–8833 (1987).

Spinas et al., "Induction of Plasma Inhibitors of Interleukin 1 and TNF–Alpha Activity by Endotoxin Administration to Normal Humans," *Am. J. Physiol.* 259:R993–R997 (1990).

Stauber et al., "Characterization and Affinity Cross–Linking of Receptors for Human Recombinant Lymphotoxin (Tumor Necrosis Factor–Beta) on a Human Histiocytic Lymphoma Cell Line U–937," *J. Biol. Chem.* 264(6):3573–3576 (1989).

Suffys et al., "Involvement of a Serine Protease in Tumor–Necrosis–Factor–Mediated Cytotoxicity," *Eur. J. Biochem.* 178:257–265 (1988).

Suggs et al., "Use of Synthetic Oligonucleotides as Hybridization Probes: Isolation of Cloned cDNA Sequences for Human β2–Microglobulin," *Proc. Natl. Acad. Sci. U.S.A.* 78(11):6613–6617 (1981).

The Cytokine Factsbook, Callard (ed.), Academic Press Inc., San Diego, CA., pp. 244–246 (1994).

Tracey et al., "Anti–Cachectin/TNF Monoclonal Antibodies Prevent Septic Shock During Lethal Bacteraemia," *Nature* 330:662–664 (1987).

Tracey et al., "Cachectin/Tumor Necrosis Factor Induces Cachexia, Anemia, and Inflammation," *J. Exp. Med.* 167:1211–1227 (1988).

Tracey et al., "Metabolic Effects of Cachectin/Tumor Necrosis Factor Are Modified by Site of Production," *J. Clin. Invest.* 86:2014–2024 (1990).

Tracey et al., "Physiological responses to cachectin," Tumor necrosis factor and related cytotoxins. *Wiley, Chichester (Ciba Foundation Symposium 131)*, pp. 88–108 (1987).

Tsujimoto et al., "Characterization and Affinity Crosslinking of Receptors for Tumor Necrosis Factor on Human Cells," *Archives of Biochem. & Biophys.* 249(2):563–568 (1968).

Unglaub et al., "Downregulation of Tumor Necrosis Factor (TNF) Sensitivity Via Modulation of TNF Binding Capacity by Protein Kinase C Activators," *J. Exp. Med.* 166:1788–1797 (1987).

Vilcek et al., "Tumor Necrosis Factor: Receptor Binding and Mitogenic Action in Fibroblasts", *Journal of Cellular Physiology Supplement* 5:57–61 (1987).

Vitt et al., "Biological and Structural Characterization of the Tumor Necrosis Factor Receptor on Multiple Cell Types: Relationship to Function", Fed. Proc. 78th Annual Meeting of the American Society of Biological Chemists 46 (6):2117 (Abstract 1118) (1987).

Wallach et al., "Cell Surface and Soluble TNF Receptors", Tumor Necrosis Factor: Structure–Function Relationship and Clinical Application, Osawa T, Bonavida B (eds) Basel, Karger, 47–57 (1992).

Wallach et al., "Mechanisms Which Take Part in Regulation of the Response to Tumor Necrosis Factor," *Lymphokine Research* 8(3):359–363 (1989).

Wallach, David, "Preparations of Lymphotoxin Induce Resistance to Their Own Cytotoxic Effect," *J. Immunol.* 132(5):2464–2469 (1984).

Wallach et al., "Regulation of the Response to Tumor Necrosis Factor," Bonavida, Gifford, Kirchner, Old (eds), *Tumor Necrosis Factor/Cachectin and Related Cytokines Int. Conf. Tumor Necrosis Factor and Related Cytotoxins, Heidelberg 1987*, pp. 134–147 (1988).

Walsh et al., "Isolation and Purification of ILS, an Interleukin 1 Inhibitor Produced by Human Gingival Epithelial Cells," *Clin. Exp. Immunol.* 68:366–374 (1987).

Weber et al., "Production of an Epidermal Growth Factor Receptor–Related Protein," *Science* 224:294–297 (1984).

Yoshie et al., "Binding and Crosslinking of $^{125}$I–Labeled Recombinant Human Tumor Necrosis Factor to Cell Surface Receptors," *J. Biochem.* 100:531–541 (1986).

Zeigler, Elizabeth J., "Tumor Necrosis Factor in Humans," *New Engl. J. Med.* 318(23):1533–1535 (1988).

\* cited by examiner

PEGYLATION REAGENTS AND COMPOUNDS FORMED THEREWITH

CROSS REFERENCE TO RELEATED APPLICATIONS

This application is a continuation-in-part of U.S. patent application Ser. No. 07/850,675, filed Mar. 13, 1992, now abandoned, which is a continuation-in-part of abandoned U.S. patent application Ser. No. 07/669,862, filed Mar. 15, 1991, which is a continuation-in-part of abandoned U.S. patent application Ser. No. 07/555,274, filed Jul. 19, 1990 and a continuation-in-part of Ser. No. 07/506,522 now U.S. Pat. No. 5,075,222, issued Dec. 24, 1991, all of which are incorporated herein by reference.

FIELD OF THE INVENTION

This invention relates to active derivatives of polyethylene glycol and related hydrophilic polymers and to methods for their synthesis for use in modifying the characteristics of surfaces and molecules. The invention also relates to polypeptides that have been covalently bonded to such active derivatives and methods for making the same.

BACKGROUND OF THE INVENTION

Polyethylene glycol ("PEG") has been studied for use in pharmaceuticals, on artificial implants, and other applications where biocompatibility is of importance. Various derivatives of PEG have been proposed that have an active moiety for permitting PEG to be attached to pharmaceuticals and implants and to molecules and surfaces generally. For example, PEG derivatives have been proposed for coupling PEG to surfaces to control wetting, static buildup, and attachment of other types of molecules to the surface, including proteins or protein residues.

PEG derivatives have also been proposed for affinity partitioning, for example, of enzymes from a cellular mass. In affinity partitioning, the PEG derivative includes a functional group for reversible coupling to an enzyme that is contained within a cellular mass. The PEG and enzyme conjugate is separated from the cellular mass and then the enzyme is separated from the PEG derivative, if desired.

In still further examples, coupling of PEG derivatives ("PEGylation") is desirable to overcome obstacles encountered in the clinical use of biologically active molecules. Published PCT Publication No. WO 92/16221 states, for example, that many potentially therapeutic proteins have been found to have a short half life in the blood serum. For the most part, proteins are cleared from the serum through the kidneys. The systematic introduction of relatively large quantities of proteins, particularly those foreign to the human system, can give rise to immunogenic reactions that, among other problems, may lead to rapid removal of the protein from the body through formation of immune complexes. For other proteins, solubility and aggregation problems have also hindered the optimal formulation of the protein.

PEGylation decreases the rate of clearance from the bloodstream by increasing the apparent molecular weight of the molecule. Up to a certain size, the rate of glomerular filtration of proteins is inversely proportional to the size of the protein. The ability of PEGylation to decrease clearance, therefore, is generally not a function of how many PEG groups are attached to the protein, but the overall molecular weight of the altered protein. Decreased clearance can lead to increased efficiency over the non-PEGylated material. See, for example, Conforti et al., *Pharm. Research Commun.* vol. 19, pg. 287 (1987) and Katre et al., *Proc. Natl. Acad. Sci. U.S.A.* vol. 84, pg. 1487 (1987).

In addition, PEGylation can decrease protein aggregation (Suzuki et al., *Biochem. Biophys. Acta* vol. 788, pg. 248 (1984)), alter protein immunogenicity (Abuchowski et al., *J. Biol. Chem.* vol. 252 pg. 3582 (1977)), and increase protein solubility as described, for example, in PCT Publication No. WO 92/16221.

PEGylation of proteins illustrates some of the problems that have been encountered in attaching PEG to surfaces and molecules. The vast majority of PEGylating reagents react with free primary amino groups of the polypeptide. Most of these free amines are the epsilon amino group of lysine amino acid residues. Typical proteins possess a large number of lysines. Consequently, random attachment of multiple PEG molecules often occurs leading to loss of protein activity.

In addition, if the PEGylated protein is intended for therapeutic use, the multiple species mixture that results from the use of non-specific PEGylation leads to difficulties in the preparation of a product with reproducible and characterizable properties. This non-specific PEGylation makes it difficult to evaluate therapeutics and to establish efficacy and dosing information. The site selective PEGylation of such proteins could lead to reproducibly-modified materials that gain the desirable attributes of PEGylation without the loss of activity.

The need to reproducibly create complexes of two or more linked bioactive molecules or compounds also exists. In certain cases, the administration of multimeric complexes that contain more than one biologically active polypeptide or drug leads to synergistic benefits. For example, a complex containing two or more identical binding polypeptides may have substantially increased affinity for the ligand or active site to which it binds relative to the monomeric polypeptide. Alternatively, a complex comprised of (1) a bioactive protein that exerts its effect at a particular site in the body and (2) a molecule that can direct the complex to that specific site may be particularly beneficial.

A need also exists for hydrolytically-stable activated polymers which form linkages which are also hydrolytically stable. Otherwise, in certain cases, the reactive group can be rendered inactive before the desired reaction takes place or the conjugate formed after reaction has a short half life in aqueous media, such as blood or plasma.

For example, Zalipsky U.S. Pat. No. 5,122,614 describes that PEG molecules activated with an oxycarbonyl-N-dicarboximide functional group that can be attached under aqueous, basic conditions by a urethane linkage to the amine group of a polypeptide. Activated PEG-N-succinimide carbonate is said to form stable, hydrolysis-resistant urethane linkages with amine groups. The amine group is shown to more reactive at basic pHs of about 8.0 to 9.5, and reactivity falls off sharply at lower pHs. Hydrolysis of the uncoupled PEG derivative, however, also increases sharply at pHs of 8.0 to 9.5. Zalipsky avoids the problem of an increase in the rate of reaction of the uncoupled PEG derivative with water by using an excess of PEG derivative to bind to the protein. By using an excess of PEG derivative, sufficient reactive amino sites are bound to PEG to modify the protein before the PEG derivative becomes hydrolyzed and unreactive.

Zalipsky's method is adequate for nonspecific attachment of the lysine fraction of a protein to a PEG derivative at one active site on the PEG. If the rate of hydrolysis of the PEG derivative is substantial, however, then it can be problematic to provide attachment at more than one active site on the PEG molecule, since a simple excess does not slow the rate of hydrolysis.

For example, a linear PEG with active sites at each end will attach to protein at one end but the reactive site at the other end can react with water to form a relatively nonreactive hydroxyl moiety instead of a PEG linking two protein groups. A similar problem arises if it is desired to couple a molecule to a surface by a PEG linking agent because the PEG is first attached to the surface or couples to the molecule, and the opposite end of the PEG derivative must remain active for a subsequent reaction. If hydrolysis is a problem, then the opposite end typically becomes inactivated.

Zalipsky U.S. Pat. No. 5,122,614 also describes several other PEG derivatives from prior patents. PEG-succinoyl-N-hydroxysuccinimide ester is said to form ester linkages that have limited stability in aqueous media. PEG-cyanuric chloride is said to be toxic and is non-specific for reaction with particular functional groups on a protein which can lead to protein inactivation. PEG-phenylcarbonate is said to produce toxic hydrophobic phenol residues that have an affinity for proteins. PEG activated with carbonyldiimidizole is said to be too slow in reacting with protein functional groups, requiring long reaction times to obtain sufficient modification of the protein.

Still other PEG derivatives have been proposed for attachment to functional groups other than the epsilon amino group of lysine. Maleimide, for example, is specific for cysteine sulfhydryl but the maleimide functionality is subject to hydrolysis.

Accordingly, a need exists for reagents and methods for reproducibly creating complexes whose parts are linked by nonantigenic, highly soluble, biologically inert molecules. The present invention satisfies the need for such complexes and provides related advantages. The present invention also satisfies the need for hydrolytically stable reagents that form hydrolytically stable conjugates.

SUMMARY OF THE INVENTION

The present invention relates to biologically-active conjugates containing a biologically-active molecule having a reactive thiol moiety and a non-peptidic polymer having an active sulfone moiety which forms a link with the reactive thiol moiety. The biologically-active molecule can be a synthetic, a naturally occurring, or a modified naturally occurring molecule. A molecule possessing the desired biological activity can be modified to contain a reactive thiol moiety.

Particularly useful biologically active molecules include the tumor necrosis factor ("TNF") inhibitors, Interleukin-1 receptor antagonists ("IL-1ra's"), CR1, exon six peptide of PDGF, and the Interleukin-2 ("IL-2") inhibitors and receptors ("IL-2r").

The polymer of the present invention contains at least one active sulfone moiety and has the formula P—SO$_2$—C—C*—, where P is polymer and C* is a reactive site for linkage with thiol moieties. The link between the thiol and activated sulfone is at Cu and can be represented by the formula P—SO$_2$—C—C*S—R, where R is the biologically-active molecule. Useful activated sulfone moieties include, for example, vinyl sulfone and chloroethyl sulfone.

Various polymers can be activated for use in all embodiments of the present invention including water soluble polymers such as polyethylene glycol ("PEG") and related hydrophilic polymers.

The present invention also provides methods of using sulfone-activated polymers to make the biologically-active conjugates discussed above. The method includes the steps of:

(a) reacting the biologically-active molecule having a reactive thiol moiety with a non-peptidic polymer having an active sulfone moiety to form a conjugate; and (b) isolating the conjugate.

Pharmaceutical compositions containing the conjugates are also within the scope of the invention.

The present invention further relates to sulfone-activated polymers useful for coupling to a variety of molecules, compounds, and surfaces. The activated sulfone moiety is the same as discussed above. Particularly useful activated polymers include bifunctional PEG derivatives activated with a sulfone moiety at one site on the PEG molecule and an NHS-ester or a maleimide functionality at another site.

Further included in the present invention are substantially purified biologically-active compounds having the formula $R_1$—X—$R_2$, called a "dumbbell" where at least one of $R_1$ or $R_2$ is a biologically-active molecule which retains its biological activity when part of the compound. The biologically-active molecule has a reactive thiol moiety which forms a link with a Michael acceptor group on a non-peptidic polymer. Biologically-active molecules suitable for use in the present invention include those mentioned above. Useful Michael acceptor groups include, for example, vinyl sulfone and maleimide. Polymers which can be activated with Michael acceptor functional groups include the water soluble polymers mentioned above.

$R_1$ and $R_2$ can be the same or different moieties. When the R groups are the same, the compound is a homodumbbell; when the R groups are different, the compound is a heterodumbbell. Particularly useful homodumbbells include, for example, PEG-linked TNF inhibitors and PEG-linked IL-1ra's. Useful heterodumbbells include, for example, those formed from IL-2r-α and IL-2r-β, heterodumbbells which inhibit the classical pathway of the complement system, and heterodumbbells formed from IL-1ra and exon 6 of PDGF.

Methods of making the dumbbell compounds are within the scope of the invention. The methods of making a dumbbell, $R_1$—X—$R_2$, include the steps of:

(a) reacting X with $R_1$ and $R_2$ to form $R_1$—X—$R_2$; and (b) purifying $R_1$—X—$R_2$.

Step (a) in the above methods of making dumbbells can further include the following steps:

protecting one reactive group of X to form a protected group on X;

reacting X having a protected group with $R_1$ to form $R_1$—X;

deprotecting the protected group on X; and reacting $R_1$—X with $R_2$ to form $R_1$—X—$R_2$.

Alternatively or in addition, step (a) can further include the following steps:

reacting an excess of X with $R_1$ to form $R_1$—X; and reacting $R_1$—X with $R_2$ to form $R_1$—X—$R_2$.

Pharmaceutical compositions containing the substantially purified compounds $R_1$—X—$R_2$ are also within the scope of the invention.

DETAILED DESCRIPTION

The present invention provides biologically-active conjugates containing (1) a biologically-active molecule having a reactive thiol moiety, and (2) a non-peptidic polymer having an active sulfone moiety which forms a linkage with the thiol moiety of the biologically-active molecule.

A "conjugate" means a complex that is formed by joining a biologically-active molecule, having an active thiol moiety, to a non-peptidic polymer, having an active sulfone moiety, via a linkage between the thiol and sulfone. As stated above, the conjugates of the present invention are biologically active.

"Biologically active" means capable of exerting a biological effect, in vitro or in vivo. A biologically active molecule includes, but is not limited to, any compound that can induce a biological effect on interaction with a natural biological molecule or on a biological system such as a cell or organism. Ways of demonstrating biological activity include in-vitro bioassays, many of which are well known in the art. For example, one can measure the biological activity of tumor necrosis factor ("TNF") inhibitors by determining if the inhibitors bind to TNF or if the inhibitors block TNF-mediated lysis of certain cells. The latter bioassay is set forth in published European Patent Application No. 90113673.9, which is specifically incorporated herein by reference.

Biologically-active molecules include, but are not limited to, pharmaceuticals, vitamins, nutrients, nucleic acids, amino acids, polypeptides, enzyme co-factors, steroids, carbohydrates, organic species such as heparin, metal containing agents, receptor agonists, receptor antagonists, binding proteins, receptors or portions of receptors, extracellular matrix proteins, cell surface molecules, antigens, haptens, targeting groups, and chelating agents. All references to receptors include all forms of the receptor whenever more than a single form exists.

"Polypeptides" and "proteins" are used herein synonymously and mean any compound that is substantially proteinaceous in nature. However, a polypeptidic group may contain some non-peptidic elements. For example, glycosylated polypeptides or synthetically modified proteins are included within the definition. "Targeting groups" can direct a compound to a location in a biological system. Binding proteins and receptors can be described by their affinity for a certain ligand.

Many polypeptides useful in the present invention are set forth in published PCT Publication No. WO 92/16221, specifically incorporated herein by reference. These proteins are well known in the art. Particularly useful polypeptides are the TNF binding proteins, also called TNF inhibitors. A "TNF binding protein" is defined herein to mean a protein that binds TNF.

One TNF binding protein ("TNFbp") is the extracellular portion of the p55 TNF receptor or the TNF receptor I. In vivo, the extracellular portion of the receptor is shed and circulates in the bloodstream as a 30 kDa glycosylated protein which binds to TNF. This binding protein is also referred to TNFbp-I or the 30 kDa TNFbp. The purification and amino acid and nucleic acid sequences of this TNF binding protein are set forth in published European Patent Application No. 90 113 673.9, which is incorporated herein by reference.

This published reference also teaches the recombinant production of glycosylated and deglycosylated forms of this TNF inhibitor. Although the actual molecular weight of the deglycosylated form of this inhibitor is approximately 18 kDa, the term "30 kDa TNF inhibitor" includes the glycosylated and deglycosylated forms.

As used herein, the terms "naturally-occurring," "native," and "wild-type" are synonymous.

European Patent Application No. 90 113 673.9, incorporated herein by reference, also sets forth the purification and amino acid and nucleic acid sequences of another TNF inhibitor, called the 40 kDa TNF inhibitor. Also called TNFbp-II, this inhibitor, in its naturally-occurring form, is the glycosylated extracellular portion of the p75 or p85 TNF receptor. European Patent Application No. 90 112 673.9 also teaches the recombinant production of the glycosylated and deglycosylated forms of this "40 kDa" inhibitor. The nucleic and amino acid sequences of the native 40 kDa TNF inhibitor are set forth in this published reference. Although the molecular weight of the deglycosylated form is not 40 kDa, both the glycosylated and deglycosylated forms of this TNFbp are referred to as "40 kDa TNF inhibitor."

European Patent Application No. 90 112 673.9, incorporated herein by reference, further teaches the recombinant production of two TNF inhibitors which are portions of the full length "40 kDa" binding protein. These two truncates are called the "Δ51" and "Δ53" TNF inhibitors. The amino acid and nucleic acid sequences of the Δ51 and Δ53 inhibitors are set forth in this published reference.

Other particularly useful polypeptides include the interleukin-1 receptor antagonists ("IL-1ra's"), as described in U.S. Pat. No. 5,075,222, incorporated herein by reference, insulin-like growth factor binding proteins ("IGFbps"), CTLA4, and exon six of platelet derived growth factor ("PDGF"), glial derived neurotrophic factor ("GDNF"), ciliary neurotrophic factor ("CNTF"), interleukin-4 receptor ("IL-4r"), and inhibitors, and interleukin-1 receptor ("IL-2r"). The nucleic acid encoding the naturally occurring IL-1ra and a method for expressing the protein in *E. Coli.* are set forth in U.S. Pat. No. 5,075,222 of Hannum et al.

Characteristics of the IL-2 receptors and CR1, the nucleic acids encoding them, and methods for their production are discussed in published PCT Publication No. WO 92/16221, specifically incorporated herein by reference.

The biologically-active molecules linked to polymers in the conjugates of the present invention have a reactive thiol moiety prior to forming the linkage. A "reactive thiol moiety" means a —SH group capable of reacting with the activated polymers as described herein.

An example of a reactive thiol is the —SH of the amino acid cysteine. Many proteins do not have free cysteines (cysteines not involved in disulfide bonding) or any other reactive thiol group. In addition, the cysteine thiol may not be appropriate for linkage to the polymer because the thiol is necessary for biological activity. In addition, proteins must be folded into a certain conformation for activity. In the active conformation, a cysteine can be inaccessible for reaction with sulfone because it is buried in the interior of the protein. Moreover, even an accessible cysteine thiol which is not necessary for activity can be an inappropriate site to form a linkage to the polymer. Amino acids not essential for activity are termed "nonessential." Nonessential cysteines can be inappropriate conjugation sites because the cysteine's position relative to the active site results in the polypeptide becoming inactive after conjugation to polymer. Like proteins, many other biologically-active molecules have reactive thiols which, for reasons similar to those recited above, are not suitable for conjugation to the polymer or contain no reactive thiol groups.

Accordingly, the present invention contemplates the introduction of reactive thiol groups into a biologically-active molecule when necessary or desirable. Thiol groups can also be introduced into an inactive molecule to form a biologically-active molecule as long as the thiol-sulfone link does not destroy the desired activity.

Reactive thiol groups can be introduced by chemical means well known in the art. Chemical modification can be used with polypeptides or non-peptidic molecules and includes the introduction of thiol alone or as part of a larger group, for example a cysteine residue, into the molecule. An example of chemically introducing thiol is set forth in Jue, R. et al., *Biochemistry*, 17, pp. 5399–5406 (1978). One can also generate a free cysteine in a polypeptide by chemically reducing cystine with, for example, DTT.

Polypeptides which are modified to contain an amino acid residue in a position where one was not present in the native protein before modification is called a "mutein." To create cysteine muteins, a nonessential amino acid can be substituted with a cysteine or a cysteine residue can be added to the polypeptide. Potential sites for introduction of a non-native cysteine include glycosylation sites and the N or C terminus of the polypeptide. The mutation of lysine to cysteine is also appropriate because lysine residues are often found on the surface of a protein in its active conformation. In addition, one skilled in the art can use any information known about the binding or active site of the polypeptide in the selection of possible mutation sites.

One skilled in the art can also use well known recombinant DNA techniques to create cysteine muteins. One can alter the nucleic acid encoding the native polypeptide to encode the mutein by standard site directed mutagenesis. Examples of standard mutagenesis techniques are set forth in Kunkel, T. A., *Proc. Nat. Acad. Sci.*, Vol. 82, pp. 488–492 (1985) and Kunkel, T. A. et al., *Methods Enzymol.*, Vol. 154, pp. 367–382 (1987), both of which are incorporated herein by reference. Alternatively, one can chemically synthesize the nucleic acid encoding the mutein by techniques well known in the art. DNA synthesizing machines can be used and are available, for example, from Applied Biosystems (Foster City, Calif.). The nucleic acid encoding the desired mutein can be expressed in a variety of expression systems, including animal, insect, and bacterial systems.

When the mutein is recombinantly produced in a bacterial expression system, the following steps are performed:

1) The nucleic acid encoding the desired mutein is created by site directed mutagenesis of the nucleic acid encoding the native polypeptide;
2) The nucleic acid encoding the desired mutein is expressed in a bacterial expression system;
3) The mutein is isolated from the bacteria and purified;
4) If not folded properly, the mutein is refolded in the presence of cysteine or another sulphydryl containing compound;
5) The refolded mutein is isolated and purified;
6) The purified and refolded target mutein is treated with a mild reducing agent;
7) The reaction mixture is dialyzed in the absence of oxygen.

As discussed below, the mutein can be isolated from the reaction mixture prior to conjugation with polymer but need not be. A reducing agent particularly useful in step 6 is dithiothreitol ("DTT") or Tris-(carboxyethylphosphine) ("TCEP"). TCEP is useful because it does not have to be removed before conjugation with a thiol-specific PEG reagent. See Burns, J. A. et al., *J. Org. Chem.*, Vol.56, No. 8, pp. 2648–2650 (1991).

After creation of the desired mutein, one skilled in the art can bioassay the mutein and compare activity of the mutein relative to the native polypeptide. As more fully discussed below, even if the relative activity of the mutein is diminished, the conjugate formed from the mutein can be particularly useful. For example, the conjugate can have increased solubility, reduced antigenicity or immunogenicity, or reduced clearance time in a biological system relative to the unconjugated molecule. Such improvements in the pharmacokinetic performance of the biologically-active molecule can increase the molecule's value in various therapeutic applications. Increased solubility can also improve the value of the molecule for in-vitro diagnostic applications.

Table 1 lists muteins of IL-1ra that have been produced. The preparation and purification of IL-1ra muteins are set forth in published PCT Patent Publication No. WO 92/16221, specifically incorporated herein by reference. The residue numbering is based upon the sequence set forth in that published application with "0" denoting addition of an amino acid at the N-terminus; "c" referring to cysteine and "s" referring to serine. For example, "c0s116" means a cysteine was inserted at the N terminus and a serine was inserted at position 116. Native IL-1ra has free cysteine residues at positions 66, 69, 116 and 122.

TABLE 1

| MUTEINS OF IL-1ra | |
| --- | --- |
| c0s116 | c0 |
| c84s116 | c6 |
| c8s116 | c8 |
| c9s116 | c9 |
| c141s116 | c141 |

Table 2 shows muteins of the 30 kDa TNF inhibitor which have also been prepared. The native 30 kDa TNF inhibitor, unlike IL-1ra, does not have any free cysteine residues. These muteins have been prepared as set forth in published PCT Publication No. WO 92/16221, specifically incorporated herein by reference, and the numbering is based upon the amino acid sequence set forth therein.

TABLE 2

| MUTEINS OF 30kDa TNF INHIBITOR |
| --- |
| c105 30kDa TNF inhibitor |
| c1 30kDa TNF inhibitor |
| c14 30kDa TNF inhibitor |
| c111 30kDa TNF inhibitor |
| c161 30kDa TNF inhibitor |

The muteins and other polypeptides of the present invention include allelic variations in the protein sequence and substantially equivalent proteins. "Substantially equivalent," means possessing a very high degree of amino acid residue homology (*See generally*, M. Dayhoff, *Atlas of Protein Sequence and Structure*, vol. 5, p. 124 (1972), National Biochemical Research Foundation, Washington, D.C., specifically incorporated herein by references) as well as possessing comparable biological activity. Also included within the scope of this invention are truncated forms of the native polypeptide or mutein that substantially retain the biological activity of the native polypeptide or mutein.

The conjugates of the present invention contain, in addition to biologically-active molecules having reactive thiol moieties, non-peptidic polymeric derivatives having active sulfone moieties. "Non-peptidic" means having less than 50% by weight of α amino acid residues.

The polymer portion of the polymeric derivative can be, for example, polyethylene glycol ("PEG"), polypropylene glycol ("PPG"), polyoxyethylated glycerol ("POG") and other polyoxyethylated polyols, polyvinyl alcohol ("PVA) and other polyalkylene oxides, polyoxyethylated sorbitol, or polyoxyethylated glucose. The polymer can be a homopolymer, a random or block copolymer, a terpolymer based on the monomers listed above, straight chain or branched, substituted or unsubstituted as long as it has at least one active sulfone moiety. The polymeric portion can be of any length or molecular weight but these characteristics can affect the biological properties. Polymer average molecular weights particularly useful for decreasing clearance rates in pharmaceutical applications are in the range of 2,000 to 35,000 daltons. In addition, if two groups are linked to the polymer, one at each end, the length of the polymer can impact upon the effective distance, and other spatial relationships, between the two groups. Thus, one skilled in the art can vary the length of the polymer to optimize or confer the desired biological activity. If the polymer is a straight chain PEG, particularly useful lengths of polymers, represented by $(Z)_n$, where Z is the monomeric unit of the polymer, include n having a range of 50–500. In certain embodiments of the present invention, n is greater than 6 and preferably greater than 10.

Monomethoxy polyethylene glycol is designated here as mPEG. The term "PEG" means any of several condensation polymers of ethylene glycol. PEG is also known as polyoxyethylene, polyethylene oxide, polyglycol, and polyether glycol. PEG can also be prepared as copolymers of ethylene oxide and many other monomers. For many biological or biotechnical applications, substantially linear, straight-chain vinyl sulfone activated PEG will be used which is substantially unsubstituted except for the vinyl sulfone.

PEG is useful in biological applications for several reasons. PEG typically is clear, colorless, odorless, soluble in water, stable to heat, inert to many chemical agents, does not hydrolyze, and is nontoxic. PEGylation can improve pharmacokinetic performance of a molecule by increasing the molecule's apparent molecular weight. The increased apparent molecular weight reduces the rate of clearance from the body following subcutaneous or systemic administration. In many cases, PEGylation can decrease antigenicity and immunogenicity. In addition, PEGylation can increase the solubility of a biologically-active molecule.

The polymeric derivatives of the present invention have active sulfone moieties. "Active sulfone" means a sulfone group to which a two carbon group is bonded having a reactive site for thiol-specific coupling on the second carbon from the sulfone group at about pH 9 or less. Examples of active sulfones include, but are not limited to, vinyl sulfone and activated ethyl sulfone. An example of an active ethyl sulfone is —$SO_2$—$CH_2$—$CH_2$—Z where Z is halogen or another leaving group capable of substitution by thiol to form the sulfone-thiol linkage —$SO_2$—$CH_2$—$CH_2$—R, where R represents a biologically active molecule. The sulfone-activated polymer can be further substituted as long as the thiol-specific reactivity at the second carbon is maintained at about pH 9 or less.

The sulfone-activated polymers of the present invention can be synthesized in at least four steps. Briefly, the first step is to increase the reactivity of a site on the polymer, typically an end group, by, for example, activation or substitution. The second step is to link sulfur directly to a carbon atom in the polymer in a form that can be converted to an ethyl sulfone or ethyl sulfone derivative having similar reactive properties. In the third step, the sulfur is oxidized to sulfone. In the fourth step, the second carbon from the sulfone group is activated.

The synthesis of a sulfone-activated polymer is described in more detail below using the synthesis of a sulfone-activated PEG as an example. The first step is the hydroxyl activation of an hydroxyl moiety in the PEG. The term "hydroxyl activation" should be interpreted herein to mean substitution as well as esterification and other methods of hydroxyl activation. Typically, in hydroxyl activation, an acid or an acid derivative such as an acid halide is reacted with the PEG to form a reactive ester in which the PEG and the acid moiety are linked through the ester linkage. The acid moiety generally is more reactive than the hydroxyl moiety. Typical esters are the sulfonate, carboxylate, and phosphate esters.

Sulfonyl acid halides that are suitable for use in the invention include, for example, methanesulfonyl chloride (also known as mesyl chloride) and p-toluene-sulfonyl chloride (also known as tosyl chloride). Methanesulfonate esters are sometimes referred to as mesylates. Toluenesulfonate esters are sometimes referred to as tosylates.

In a substitution type of hydroxyl activation, the entire hydroxyl group on the PEG is substituted by a more reactive moiety, typically a halide. For example, thionyl chloride, can be reacted with PEG to form a more reactive chlorine substituted PEG.

Thus, when PEG is the starting material, the typical reaction product of the first step is an ester or halide-substituted PEG.

In the second step, the ester or halide is substituted by an alcohol which contains a reactive thiol attached to an ethyl group, a thioethanol moiety. Thioethanol is an example of a suitable alcohol. In this step, the sulfur in the thiol is bonded directly to a carbon on the polymer.

Next, in the third step, the sulfur is oxidized to sulfone. Useful oxiding agents include, for example, hydrogen peroxide, sodium perborate, or peroxy acids.

In the fourth step, the hydroxyl moiety of the alcohol used in step two is activated. This step is similar to the first step in the reaction sequence. Substitution typically is with halide to form a haloethyl sulfone or a derivative thereof having a reactive site on the second carbon removed from the sulfone moiety. Typically, the second carbon on the ethyl group will be activated by a chloride or bromide halogen. Hydroxyl activation should provide a site of similar reactivity, such as the sulfonate ester. Suitable reactants are, for example, the acids, acid halides, and others previously mentioned in discussing the first step in the reaction. Thionyl chloride is particularly useful for substitution of the hydroxyl group with the chlorine atom.

The resulting polymeric activated ethyl sulfone is stable, isolatable, and suitable for thiol-selective coupling reactions. PEG chloroethyl sulfone is stable in water at a pH of about 7 or less, but nevertheless can be used to advantage for thiol-selective coupling reactions at conditions of basic pH up to at least about pH 9. At a pH of above about 9, the thiol selectivity is diminished and the sulfone moiety becomes somewhat more reactive with amino groups. The linkage formed upon reaction with thiol is also hydrolytically stable.

In a fifth step that can be added to the synthesis, the activated ethyl sulfone is reacted with a base to from PEG vinyl sulfone or one of its active derivatives for thiol-selective coupling. Suitable bases include, for example, sodium hydroxide or triethylamine. Like activated ethyl sulfones, vinyl sulfone is hydrolytically stable, isolatable, thiol-selective, and forms hydrolytically-stable linkages upon reaction with thiol.

As used herein, "hydrolytically stable" means that the linkage between the polymer and the sulfone moiety and between the sulfone-thiol after conjugation does not react with water at a pH of less than about 11 for at least three days. Hydrolytic stability is desirable because, if the rate of hydrolysis is significant, the polymer can be deactivated before the reaction between polymer and the thiol of the biologically-active molecule takes place.

As mentioned above, for example, a linear PEG with active sites at each end will attach to a protein at one end, but, if the rate of hydrolysis is significant, will react with water at the other end to become capped with a relatively nonreactive hydroxyl moiety, rather than forming a "dumbbell" molecular structure with attached proteins or other desirable groups on each end. A similar problem arises when coupling a molecule to a surface by a PEG linking agent because the PEG is first attached to the surface or couples to the molecule, and the opposite end of the PEG derivative must remain active for a subsequent reaction. If hydrolysis is a problem, then the opposite end typically becomes inactivated.

Alternatively, the sulfone-activated derivatives can be prepared by attaching a linking agent having a sulfone moiety to a PEG (or other polymer) activated with a different functional group. For example, an amino activated PEG can be reacted under favorable conditions of pH of about 9 or less with a small molecule that has a succinimidyl active ester moiety at one terminus and vinyl sulfone at the other terminus. The amino-activated PEG forms a stable linkage with the succinimidyl ester. The resulting PEG is activated with the vinyl sulfone at the terminus and is hydrolytically stable: $PEG-NH-OC-CH_2-CH_2-SO_2CH=CH_2$.

A similar activated PEG can be achieved by reacting an amine-reactive PEG such as succinimidyl active ester PEG, $PEG-CO_2-NHS$, with a small molecule that has an amine moiety at one terminus and a vinyl sulfone moiety at the other terminus.

PEG chloroethyl sulfone and PEG vinyl sulfone were prepared as set forth in Example 1. Thiol-selective reactivity of PEG vinyl sulfone and chloroethyl sulfone is shown in Example 2. Hydrolytic stability of the polymer-sulfone linkage of two compounds is shown in Example 3. Hydrolytic stability of the linkage between thiol and sulfone is shown in Example 16.

When the polymer does not have an hydoxyl moiety, one can first be added by chemical methods well known in the art before carrying out the steps described above.

The activated polymeric derivatives of the present invention can have more than one reactive group. The derivatives can be monofunctional, bifunctional, or multifunctional. The reactive groups may be the same (homofunctional) or different (heterofunctional) as long as there is at least one active sulfone moiety.

Two particularly useful homobifunctional derivatives are PEG-bis-chlorosulfone and PEG-bis-vinyl sulfone. One skilled in the art can synthesize those molecules using PEG having hydroxyl moieties at each end as a starting material and following the general method set forth above.

Heterobifunctional derivatives can also be synthesized. Two particularly useful heterobifunctional derivatives include, for example, a linear PEG with either a vinyl sulfone or a maleimide at one end and an N-hydroxysuccinimide ester ("NHS-ester") at the other end. The NHS-ester is amine-specific. PEG having an NHS-ester at one end and an activated sulfone moiety at the other can be attached to both lysine and cysteine residues. A stable amine linkage can be achieved, leaving the hydrolytically-stable unreacted sulfone available for subsequent reaction with thiol. Those two heterobifunctional PEG derivatives have been synthesized as described in Examples 5 and 6. If the maleimide NHS-ester heterobifunctional reagent is made using straight-chain PEG, represented by $(Z)_n$, where Z is the monomeric unit, n is greater than 6 and preferably greater than 10.

Other active groups for heterofunctional sulfone-activated PEGs can be selected from among a wide variety of compounds. For biological and biotechnical applications, the substituents would typically be selected from reactive moieties typically used in PEG chemistry to activate PEG such as the aldehydes, trifluoroethylsulfonate (sometimes called tresylate), n-hydroxylsuccinimide ester, cyanuric chloride, cyanuric fluoride, acyl azide, succinate, the p-diazo benzyl group, the 3-(p-diazophenyloxy)-2-hydroxy propyloxy group, and others.

Examples of active moieties other than sulfone are shown in Davis et al. U.S. Pat. No. 4,179,337; Lee et al. U.S. Pat. Nos. 4,296,097 and 4,430,260; Iwasaki et al. 4,670,417; Katre et al. U.S. Pat. Nos. 4,766,106; 4,917,888; and 4,931,544; Nadagawa et al. U.S. Pat. No. 4,791,192; Nitecki et al. U.S. Pat. No. 4,902,502 and 5,089,261; Saifer U.S. Pat. No. 5,080,891; Zalipsky U.S. Pat. No. 5,122,614; Shadle et al. U.S. Pat. No. 5,153, 265; Rhee et al. U.S. Pat. No. 5,162, 430; European Patent Application Publication No. 0 247 860; and PCT International Application Nos. US86/01252; GB89/01261; GB89/01262; GB89/01263; US90/03252; US90/06843; US91/06103; US92/00432; and US92/02047, the contents of which are incorporated herein by reference.

An example of a trifunctional derivative is a glycerol backbone to which three vinyl sulfone PEG moieties are attached. This molecule can be represented by the formula:

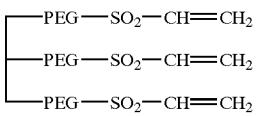

This derivative was prepared as described in Example 12.

Another example of a multifunctional derivative is the "star" molecule. Star molecules are generally described in Merrill U.S. Pat. No. 5,171,264, incorporated herein by reference. Star molecules have a core structure to which multiple PEG chains or "arms" are attached. The sulfone moieties can be used to provide an active, functional group on the end of the PEG chain extending from the core and as a linker for joining a functional group or other moiety to the star molecule arms.

It should be apparent to the skilled artisan that the activated polymers discussed above could be used to carry a wide variety of substituents and combinations of substituents.

As stated above, the conjugates of the present invention are formed by reacting thiol-containing biologically-active molecules with sulfone-activated polymers. The linkage between the thiol reactive group and the sulfone-activated polymer is a covalent bond.

A general method for preparing the conjugates of the present invention includes the following steps:

(1) Choose the desired biologically-active molecule and determine if the molecule possesses a free thiol group by means well known in the art. See, for example, Allen, G., "Sequencing of Proteins and Peptides," pp. 153–54, in *Laboratory Techniques in Biochemistry and Molecular Biology*, Work, T. S., and Burdon, R. H., eds. (1972), incorporated herein by reference. If the molecule has a free thiol, proceed to step 3. If the molecule has no free thiol, proceed to step 2.

(2) If no free thiol exists in the molecule, add thiol as discussed above. After adding thiol, perform a bioassay to determine if the desired biological activity or a portion of the biological activity is retained.

(3) Synthesize the desired sulfone-activated polymer as discussed above.

(4) React the activated polymer with the molecule having a free thiol.

(5) Isolate the reaction product using chromatographic techniques well known in the art. For protein conjugates, see, for example, Scopes, R., *Protein Purification*, Cantor, C. R. ed., Springer-Verlag, New York (1982). For nonprotein molecules, see, for example, Still, W. C. et al., *J. Org. Chem.*, 43, pp.2923–2925 (1978). If no conjugate forms, add thiol to another location on the biologically-active molecule and repeat steps (4) and (5).

(6) Determine biological activity of the conjugate formed using the relevant bioassay.

One skilled in the art can add or delete certain steps. For example, one skilled in the art might not assay bioactivity in step 2 or might presume biological activity after PEGylation based upon previous experiments. The skilled artisan can also add the step of varying the size, length, or molecular weight of the linker to optimize or confer biological activity.

Several conjugates have been prepared. The 30 kDa TNFbp c105 mutein described above was conjugated with PEG vinyl sulfone as described in Example 10. Example 8 shows that native IL-1ra, which contains four free cysteines, reacted under similar conditions. The c84 IL-1ra mutein also reacted well. Example 13 shows the conjugation of three 30 kDa TNF inhibitor muteins to three PEG chains bonded to a glycerol backbone.

The conjugates of the present invention can be used for a variety of purposes including, but not limited to, in-vitro diagnostic assays and the preparation of pharmaceutical compositions. Many of the conjugates of the present invention have at least one of the following characteristics relative to the unconjugated molecule:

(1) increased solubility in aqueous solution;
(2) reduced antigenicity or immunogenicity;
(3) reduced rate of clearance following subcutaneous or systemic administration due to increased apparent molecular weight.

Pharmaceutical preparations of conjugates containing IL-1ra are particularly useful. IL-1ra, alone or in combination with the 30 kDa TNF binding protein, can be used to treat arthritis, inflammatory bowel disease, septic shock, ischemia injury, reperfusion injury, osteoporosis, asthma, insulin diabetes, myelogenous and other leukemias, psoriasis, adult respiratory distress syndrome, cachexia/anorexia, and pulmonary fibrosis.

Conjugates containing TNF binding proteins ("TNFbps") are also particularly useful. Such conjugates can be used to treat TNF-mediated diseases such as adult respiratory distress syndrome, pulmonary fibrosis, arthritis, septic shock, inflammatory bowel disease, multiple sclerosis, graft rejection and hemorrhagic trauma.

The biologically active conjugates of the present invention can further include non-biologically active moieties.

The present invention also includes substantially purified compounds having the formula $R_1$—X—$R_2$, where at least one of $R_1$ and $R_2$ is a biologically-active molecule having a reactive thiol moiety which forms a covalent bond with X, a Michael acceptor-activated polymer. In the present invention, the biological activity of $R_1$—X—$R_2$ retains the biological activity of $R_1$ or $R_2$. Molecules having the formula $R_1$—X—$R_2$ are referred to herein as "dumbbell" molecules.

As stated above, the compounds of the present invention are substantially purified. "Substantially purified" as used herein means a "homogenous composition." A homogenous composition contains molecules of $R_1$—X—$R_2$ and is substantially free from compounds that (1) deviate in the composition of $R_1$ or $R_2$, or (2) are linked together by more than one activated polymer. The homogeneous composition can contain molecules of $R_1$—X—$R_2$ which differ in the length of X. For straight-chain polymers, represented by $(Z)_n$, where Z is the monomeric unit, n is greater than 6 and preferably greater than 10. To have a homogeneous composition, $R_1$ and $R_2$ need not be attached to X at the same location on X or on the same location on either R group.

X is a non-peptidic polymer having a first reactive group and a second reactive group. A "reactive group" is a group capable of reacting with R. At least one reactive group on X is a Michael-type acceptor. The terms "reactive group" and "functional group" are used herein synonymously. The terms "Michael acceptor" and "Michael-type acceptor" are also used herein synonymously. Polymers suitable for use in the present invention are also discussed above and include, for example, PEG, POG, and PVA.

"Michael acceptors" are functional groups susceptible to Michael addition. "Michael addition" involves a nucleophilic attack on an electrophilic center which is adjacent to a pi system, having an electronegative atom. Examples of pi systems having an electronegative atom include sulfoxide, sulfonyl, carbonyl and heterocyclic aromatics. The nucleophile adds to the electrophilic center.

Michael acceptors can be represented by the formula:

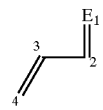

where E is an electronegative atom. Addition takes place at the 4 position to form the following:

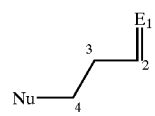

where $N_u$ represents the nucleophile now bonded to the atom at position 4. Michael acceptor functional groups include, but are not limited to, maleimide and vinyl sulfone. The activated polymer from which a dumbbell is formed can, but need not, contain a vinyl sulfone species of Michael acceptor.

Activated polymers of the present invention include PEG having two or more Michael acceptor groups, including for example, PEG-bis-vinyl sulfone and PEG-bis-maleimide. PEG-bis-vinyl sulfone has been prepared as described in Examples 7. PEG-bis-maleimide has been prepared as described in PCT Publication No. WO 92/16221, incorporated herein by reference.

At least one of $R_1$ and $R_2$ is biologically active prior to coupling to X or to X—R. "Biologically active" has the same definition recited above. As stated above, biologically active molecules include, but are not limited to, binding proteins and targeting groups.

Both $R_1$ and $R_2$ can be biologically active but need not be. In some cases, if $R_1$ and $R_2$ have an affinity for the same ligand, the dumbbell can have a greater affinity for that ligand than either $R_1$ or $R_2$ alone. Published PCT Publication No. WO 92/16221 shows that the homodumbbell containing two molecules of 30 kDa TNFbp linked by a PEG polymer is better at inhibiting cytotoxicity of TNFs in in-vitro assays than the 30 kDa molecule alone. In certain cases, $R_1$ can be a molecule which directs the compound $R_1$—X—$R_2$ to a certain location in a biological system and R2 can have an affinity for a ligand in that location.

Alternatively, only one of $R_1$ and $R_2$ can be biologically active in the compound $R_1$—X—$R_2$. The nonbiologically-active group can be a surface or any other biologically-inert molecule or compound.

In the present invention, the biologically active R group has a reactive thiol moiety. The biologically active R group can be a synthetic molecule. As used herein, the term "synthetic molecule" means a molecule to which a reactive thiol moiety has been added. Synthetic molecules include, for example, muteins containing a non-native cysteine. The thiol moiety reacts with a Michael-type acceptor of the polymer to form a covalent bond.

After formation of this covalent bond, the biologically-active molecule retains its biological activity. The R group "retains its biological activity" within the meaning of the invention if, after reaction with activated polymer, it has at least one tenth of the biological activity it had before reaction with polymer, preferably at least 40%, and more preferably at least 60%.

A general method for producing dumbbells follows:

(1) Choose an R group possessing the desired biological activity, for example, a protein such as tumor necrosis factor binding protein (TNFbp).

(2) Measure activity using the relevant bioassay.

(3) Determine the number of free sulfhydryl groups, for example, cysteine residues not involved in disulfide bonding, using generally known methods in the art. One such method is described in Allen, G., "Sequencing of proteins and peptides," pp. 153–54, in *Laboratory Techniques in Biochemistry and Molecular Biology*, Work, T. S., and Burdon, R. H., eds. (1972). If there are no free cysteines, proceed to step 4(a). If there is one free cysteine, or only one accessible to the PEGylation reagent, proceed to the reaction step in 4(c). If the protein has more than one free cysteine, go to step 5.

(4) When R is polypeptide and no free cysteines exist:
  (a) Create a mutein by inserting a cysteine or replacing a non-cysteine residue with a cysteine. Useful mutation sites include the N or C terminal ends of the protein, glycosylation sites, or lysine residues. Muteins can be routinely made, as stated above, by chemical synthesis or recombinant technology. Alternatively, chemically add a thiol moiety.
  (b) Measure activity and compare that activity with the activity measured in step 2.
  (c) If the mutein retains the activity measured in step 2, react the mutein with a polymer, such as PEG, having a single sulfhydryl-preferred reactive group. If the mutein bonds to the mono-reactive PEG (becomes PEGylated), measure activity and compare that activity with the activity measured in step 2. If the PEGylated mutein retains the activity measured in step 2, react the unPEGylated mutein with a PEG having two thiol-specific Michael Acceptors, such as bis-maleimide, to create dumbbell molecules. Repeat the bioassay to confirm that the dumbbells retain biological activity.

If one skilled in the art desires that $R_1$ and $R_2$ be different, the bis-reactive polymeric group can be reacted in series with $R_1$ and then $R_2$. Prior to reacting polymer with $R_1$, one of the two functional groups of the polymer is blocked or protected by means well known in the chemical arts to form a protected group on X. See, for example, Greene, T. W. et al., *Protective Groups in Organic Synthesis*, John Wiley and Sons, Inc. (1991), incorporated herein by reference. In this context, "protected" means the functional group is not available for reaction. When X having a protected group is reacted with $R_1$, $R_1$—X, and not $R_1$—X—$R_1$, is formed. After $R_1$—X is formed, the blocking or protecting group is removed prior to reaction with $R_2$. "Deprotected" means the protective group is removed or the functional group is otherwise made available for reaction.

Alternatively, heterodumbbells can be formed by reacting $R_1$ with an excess of the bis-activated polymer to force $R_1$—X formation. After reaction, $R_1$—X is separated from the reaction mixture using chromatographic techniques well known in the art, including, for example, ion exchange chromatography. $R_1$—X is then reacted with $R_2$ to form $R_1$—X—$R_2$.

(d) If the mutein created in step 4(a) or the PEGylated mutein formed in step 4(c) does not substantially retain biological activity, start with the native protein, create a different mutein, and repeat steps 4(b) and 4(c). In addition, the length or molecular weight of the polymer X can be changed to optimize or confer biological activity.

(5) For proteins with more than one free cysteine, monoPEGylate, bioassay, and react with the bifunctional PEGylation reagent. If higher-ordered structures are formed, i.e. more than two proteins are PEG-linked, separate the dumbbells via chromatographic methods known in the art. Where such separation is undesirable for any reason, delete or replace a free cysteine with another amino acid and proceed to step 4(b).

(6) For non-protein biologically-active R groups, exploit free sulfhydryl groups for attachment to the polymer X. Add free sulfhydryl groups to the molecule if necessary or desirable.

One skilled in the art might choose to modify, add or delete certain steps. For example, one might choose to react active proteins with a bifunctional-PEG and skip the monoPEGylation step.

Several dumbbell molecules of the present invention have been prepared. Published PCT Application No. WO 92/16221, which is incorporated herein by reference, sets forth the preparation of the following dumbbells prepared using bis-maleimido-PEG: 30 kDa TNF inhibitor homodumbbells, Il-2 inhibitor heterodumbbell, heterodumbbells which inhibit the classical pathway of the complement system, and IL-1ra and PDGF heterodumbbells.

Pharmaceutical compositions containing many of the conjugates or compounds (collectively, the "conjugates") of the present invention can be prepared. These conjugates can be in a pharmaceutically-acceptable carrier to form the pharmaceutical compositions of the present invention. The term "pharmaceutically acceptable carrier" as used herein means a non-toxic, generally inert vehicle for the active ingredient, which does not adversely affect the ingredient or the patient to whom the composition is administered. Suitable vehicles or carriers can be found in standard pharmaceutical texts, for example, in *Remington's Pharmaceutical Sciences*, 16th ed., Mack Publishing Co., Easton, Pa. (1980), incorporated herein by reference. Such carriers include, for example, aqueous solutions such as bicarbonate buffers, phosphate buffers, Ringer's solution and physiological saline. In addition, the carrier can contain other pharmaceutically-acceptable excipients for modifying or maintaining the pH, osmolarity, viscosity, clarity, color, sterility, stability, rate of dissolution, or odor of the formulation.

The pharmaceutical compositions can be prepared by methods known in the art, including, by way of an example, the simple mixing of reagents. Those skilled in the art will know that the choice of the pharmaceutical carrier and the appropriate preparation of the composition depend on the intended use and mode of administration.

In one embodiment, it is envisioned that the carrier and the conjugate constitute a physiologically-compatible, slow-release formulation. The primary solvent in such a carrier can be either aqueous or non-aqueous in nature. In addition, the carrier can contain other pharmacologically-acceptable excipients for modifying or maintaining the pH, osmolarity, viscosity, clarity, color, sterility, stability, rate of dissolution, or odor of the formulation. Similarly, the carrier can contain still other pharmacologically-acceptable excipients for modifying or maintaining the stability, rate of dissolution, release, or absorption of the conjugate. Such excipients are those substances usually and customarily employed to formulate dosages for parenteral administration in either unit dose or multi-dose form.

Once the pharmaceutical composition has been formulated, it can be stored in sterile vials as a solution, suspension, gel, emulsion, solid, or dehydrated or lyophilized powder. Such formulations can be stored either in a ready to use form or requiring reconstitution immediately prior to administration. The preferred storage of such formulations is at temperatures at least as low as 4° C. and preferably at −70° C. It is also preferred that such formulations containing the conjugates are stored and administered at or near physiological pH. It is presently believed that administration in a formulation at a high pH (i.e. greater than 8) or at a low pH (i.e. less than 5) is undesirable.

The manner of administering the formulations containing the conjugates for systemic delivery can be via subcutaneous, intramuscular, intravenous, oral, intranasal, or vaginal or rectal suppository. Preferably the manner of administration of the formulations containing the conjugates for local delivery is via intraarticular, intratracheal, or instillation or inhalations to the respiratory tract. In addition it may be desirable to administer the conjugates to specified portions of the alimentary canal either by oral administration of the conjugates in an appropriate formulation or device.

In another suitable mode for the treatment of osteoporosis and other bone loss diseases, for example, an initial intravenous bolus injection of TN inhibitor conjugate and IL-1 inhibitor conjugate is administered followed by a continuous intravenous infusion of TNF inhibitor conjugate and IL-1 inhibitor conjugate. For oral administration, the conjugate is encapsulated. The encapsulated conjugate can be formulated with or without pharmaceutically-acceptable carriers customarily used in the compounding of solid dosage forms. Preferably, the capsule is designed so that the active portion of the formulation is released at that point in the gastrointestinal tract when bioavailability is maximized and pre-systemic degradation is minimized. Additional excipients can be included to facilitate absorption of the conjugate. Diluents, flavorings, low melting point waxes, vegetable oils, lubricants, suspending agents, tablet disintegrating agents, and binders can also be employed.

Regardless of the manner of administration, the specific dose is calculated according to the approximate body weight of the patient. Other factors in determining the appropriate dosage can include the disease or condition to be treated or prevented, route of administration and the age, sex and medical condition of the pateint. In certiain embodiments, the dosage and administration is designed to create a pre-selected concentration range of the conjugate in the patient's blood stream. For example, it is believed that the maintenance of circulating concentrations of TNF inhibitor and IL-1 inhibitor of less than 0.01 ng per mL of plasma may not be an effective composition, while the prolonged maintenance of circulating levels in excess of 10 $\mu$g per mL may have undesirable side effects. Further refinement of the calculations necessary to determine the appropriate dosage for treatment involving each of the above mentioned formulations is routinely made by those of ordinary skill in the art and is within the ambit of tasks routinely performed by them without undue experimentation, especially in light of the dosage information and assays disclosed herein. These dosages may be ascertained through use of the established assays for determining dosages utilized in conjunction with appropriate dose-response data.

It should be noted that the conjugate formulations described herein may be used for veterinary as well as human applications and that the term "patient" should not be construed in a limiting manner. In the case of veterinary applications, the dosage ranges should be the same as specified above.

The following examples are illustrative of the invention and are not intended as limitations.

EXAMPLE 1

Synthesis

The reaction steps can be illustrated structurally as follows:

(1) $PEG-OH+CH_3SO_2Cl \rightarrow PEG-OSO_2CH_3$ (2) $PEG-OSO_2CH_3+HSCH_2CH_2OH \rightarrow PEG-SCH_2CH_2OH$ (3) $PEG-SCH_2CH_2OH+H_2O_2 \rightarrow PEG-SO_2CH_2CH_2OH$ (4) $PEG-SO_2CH_2CH_2OH+SOCl_2 \rightarrow PEG-SO_2CH_2CH_2Cl$ (5) $PEG-SO_2CH_2CH_2Cl+NaOH \rightarrow PEG-SO_2-CH=CH_2+HCl$ Each of the above reactions is described in detail below:

Reaction 1. Reaction 1 represents the preparation of the methane sulfonyl ester of polyethylene glycol, which can also be referred to as the methanesulfonate or mesylate of polyethylene glycol. The tosylate and the halides can be prepared by similar procedures, which are believed to be apparent to the skilled artisan.

To prepare the mesylate, twenty-five grams of PEG of molecular weight 3400 was dried by azeotropic distillation in 150 mL of toluene. Approximately half of the toluene was distilled off in drying the PEG. Forty mL of dry dichloromethane was added to the toluene and PEG solution, followed by cooling in an ice bath. To the cooled solution was added 1.23 mL of distilled methanesulfonyl chloride, which is an equivalent weight of 1.6 with respect to PEG hydroxyl groups, and 2.66 mL of dry triethylamine, which is an equivalent weight of 1.3 with respect to PEG hydroxyl groups. "Equivalent weight" as used above can be thought of as "combining weight" and refers to the weight of a compound that will react with an equivalent weight of PEG hydroxyl groups.

The reaction was permitted to run overnight during which time it warmed to room temperature. Triethylammonium hydrochloride precipitated and the precipitate was removed by filtration. Thereafter, the volume was reduced by rotary evaporation to 20 mL. The mesylate was precipitated by addition to 100 mL of cold dry ethyl ether. Nuclear magnetic resonance (NMR) analysis showed 100% conversion of hydroxyl groups to mesylate groups.

Reaction 2. Reaction 2 represents the formation of polyethylene glycol mercaptoethanol by reaction of the mesylate with mercaptoethanol. The reaction causes the methanesulfonate radical to be displaced from the PEG. The sulfur in the mercaptoethanol radical is attached directly to the carbon in the carbon-carbon backbone of the PEG.

Twenty grams of the mesylate from reaction 1 was dissolved in 150 mL of distilled water. The solution of mesylate and water was cooled by immersion in an ice bath. To the cooled solution was added 2.37 mL of mercaptoethanol, which is 3 equivalent weights with respect to PEG hydroxyl groups. Also added was 16.86 mL of 2N NaOH base. The reaction was refluxed for 3 hours, which means that the vapors rising from the heated reaction were continuously condensed and allowed to flow back into the reaction.

The polyethylene glycol mercaptoethanol product was extracted three times with dichloromethane using approximately 25 mL of dichloromethane each time. The organic fractions were collected and dried over anhydrous magnesium sulfate. The volume was reduced to 20 mL and the product was precipitated by addition to 150 mL of cold dry ether.

NMR analysis in $d_6$-DMSO (dimethyl sulfoxide) gave the following peaks for PEG—$SCH_2CH_2OH$: 2.57 ppm, triplet, —$CH_2$—S—; 2.65 ppm, triplet, —S—$CH_2$—; 3.5 ppm, backbone singlet; and 4.76 ppm, triplet, —OH. Integration of the peak for —S—$CH_2$— indicated 100% substitution.

Reaction 3. Reaction 3 represents peroxide oxidation of the polyethylene glycol mercaptoethanol product to convert the sulfur, S, to sulfone, $SO_2$. PEG-β-hydroxysulfone is produced.

Twenty grams of PEG—$SCH_2CH_2OH$ was dissolved in 30 mL of 0.123M tungstic acid solution and cooled in an ice bath. The tungstic acid solution was prepared by dissolving the acid in sodium hydroxide solution of pH 11.5 and then adjusting the pH to 5.6 with glacial acetic acid. Twenty mL of distilled water and 2.88 mL of 30% hydrogen peroxide, which has an equivalent weight of 2.5 with respect to hydroxyl groups, was added to the solution of tungstic acid and polyethylene glycol mercaptoethanol and the reaction was permitted to warm overnight to room temperature.

The oxidized product was extracted three times with dichloromethane using 25 mL of dichloromethane each time. The collected organic fractions were washed with dilute aqueous sodium bicarbonate and dried with anhydrous magnesium sulfate. The volume was reduced to 20 mL. The PEG-β-hydroxysulfone product was precipitated by addition to cold dry ethyl ether.

NMR analysis in $d_6$-DMSO gave the following peaks for PEG—$SCH_2CHOH$: 3.25 ppm, triplet, —$CH_2$—$SO_2$—; 3.37 ppm, triplet, —$SO_2$—$CH_2$—; 3.50 ppm, backbone; 3.77 triplet, —$CH_2OH$; 5.04 ppm, triplet, —OH. The hydroxyl peak at 5.04 ppm indicated 85% substitution. However, the peak at 3.37 ppm for —$SO_2$—$CH_2$— indicated 100% substitution and is considered to be more reliable.

Reaction 4. Reaction 4 represents the final step in synthesis, isolation, and characterization of polyethylene glycol chloroethyl sulfone.

To synthesize the product, twenty grams of PEG—$SO_2CH_2CH_2OH$, PEG-β-hydroxysulfone, was dissolved in 100 mL of freshly distilled thionyl chloride and the solution was refluxed overnight. The thionyl chloride had been distilled over quinoline. Excess thionyl chloride was removed by distillation. Fifty mL of toluene and 50 mL of dichloromethane were added and removed by distillation.

To isolate the product, the PEG chloroethyl sulfone was dissolved in 20 mL of dichloromethane and precipitated by addition to 100 mL of cold dry ethyl ether. The precipitate was recrystallized from 50 mL of ethyl acetate to isolate the product.

Nuclear magnetic resonance was used to characterize the product. NMR analysis of PEG—$SO_2CH_2CH_2Cl$ in $d_6$-DMSO gave the following peaks: 3.50 ppm, backbone; 3.64 ppm, triplet, —$CH_2SO_2$—; 3.80 ppm, triplet, —$SO_2$—$CH_2$—. A small hydroxyl impurity triplet appeared at 3.94 ppm. Calculation of the percentage substitution was difficult for this spectrum because of the proximity of the important peaks to the very large backbone peak.

Reaction 5. Reaction 5 represents conversion of polyethylene glycol chloroethyl sulfone from reaction step 4 to polyethylene glycol vinyl sulfone and isolation and characterization of the vinyl sulfone product.

The PEG vinyl sulfone was readily prepared by dissolving solid PEG chloroethyl sulfone in dichloromethane solvent followed by addition of two equivalents of NaOH base. The solution was filtered to remove the base and the solvent was evaporated to isolate the final product PEG—$SO_2$—$CH=CH_2$, PEG vinyl sulfone.

The PEG vinyl sulfone was characterized by NMR analysis in $d_6$-DMSO dimethyl sulfoxide. NMR analysis showed the following peaks: 3.50 ppm, backbone; 3.73 ppm, triplet, —$CH_2$—$SO_2$—; 6.21 ppm, triplet, =$CH_2$; 6.97 ppm, doublet of doublets, —$SO_2$—CH—.

The 6.97 ppm peak for —$SO_2$—CH— indicated 84% substitution. The 6.21 ppm peak for =$CH_2$ indicated 94% substitution. Titration with mercaptoethanol and 2,2'-dithiodipyridine indicated 95% substitution.

EXAMPLE 2

Thiol-selective Reactivity

Example 2 shows that PEG vinyl sulfone and its precursor PEG chloroethyl sulfone are significantly more reactive with thiol groups (—SH) than with amino groups (—$NH_2$) or imino groups (—NH—). Compounds containing thiol groups are organic compounds that resemble alcohols, which contain the hydroxyl group —OH, except that in thiols, the oxygen of the hydroxyl group is replaced by sulfur. Thiols sometimes are also called sulfhydryls or mercaptans. PEG vinyl sulfone contains the vinyl sulfone group —$SO_2$—$CH=CH_2$. PEG chloroethyl sulfone contains the chloroethyl sulfone group —$SO_2CH_2CH_2Cl$.

Selectivity for thiols is important in protein modification because it means that cysteine units (containing —SH) will be modified in preference to lysine units (containing —$NH_2$) and histidine units (containing —NH—). The selectivity of PEG vinyl sulfone for thiols means that PEG can be selectively attached to cysteine units, thus preserving protein activity for specific proteins and controlling the number of PEG molecules attached to the protein.

The relative reactivity of PEG vinyl sulfone with thiol and amino groups was determined by measuring the rates of reaction of PEG vinyl sulfone with N-α-acetyl lysine methyl ester and with mercaptoethanol. N-α-acetyl lysine methyl ester is a lysine model containing an amino group and is abbreviated Lys—NH$_2$. Mercaptoethanol serves as a cysteine model containing a thiol group and is abbreviated Cys—SH. Relative reactivity of PEG chloroethyl sulfone was similarly determined. This molecule may serve as a "protected" form of the vinyl sulfone since it is stable in acid but converts to PEG vinyl sulfone upon addition of base.

Reactivity for PEG vinyl sulfone and for the PEG chloroethyl sulfone precursor was investigated at pH 8.0, pH 9.0, and at pH 9.5. Buffers for controlling the pH were 0.1 M phosphate at pH 8.0 and 0.1 M borate at pH 9.0 and at pH 9.5. For measurement of mercaptoethanol reactivity, 5 mM ethylenediamine tetraacetic acid (EDTA) was added to both buffers to retard conversion of thiol to disulfide.

For reaction of the PEG derivatives of the invention with Lys—NH$_2$, a 3 mM solution of the PEG derivative was added under stirring to a 0.3 mM Lys—NH$_2$ solution in the appropriate buffer for each of the three levels of basic pH. The reaction was monitored by addition of fluorescamine to the reaction solution to produce a fluorescent derivative from reaction with remaining amino groups. The monitoring step was performed by adding 50 µL of reaction to 1.95 mL of phosphate buffer of pH 8.0 followed by adding 1.0 mL of fluorescamine solution under vigorous stirring. The fluorescamine solution was 0.3 mg fluorescamine per mL of acetone.

Fluorescence was measured 10 minutes after mixing. Excitation was at wavelength 390 nm. Light emission occurred at 475 nm. No reaction was observed in 24 hours for either PEG vinyl sulfone or PEG chloroethyl sulfone at pH 8.0. At pH 9.5 the reaction was slow, but all amino groups were reacted after several days.

For reaction of the PEG vinyl sulfone and PEG chloroethyl sulfone precursor with Cys—SH, a 2 mM solution of the PEG derivative was added to a 0.2 mM solution of Cys—SH in the appropriate buffer for each of the three levels of basic pH. The reaction was monitored by adding 4-dithiopyridine to the reaction solution. The 4dithiopyridine compound reacts with Cys—SH to produce 4-thiopyridone, which absorbs ultraviolet light.

The monitoring step was performed by adding 50 µL of reaction mixture to 0.95 mL of 0.1 M phosphate buffer at pH 8.0 and containing 5 mM EDTA, followed by adding one mL of 2 mM 4-dithiopyridine in the same buffer.

Absorbance of 4-thiopyridone was measured at 324 nm. Both PEG vinyl sulfone and PEG chloroethyl sulfone showed reactivity toward Cys—SH, with PEG vinyl sulfone showing greater reactivity. At pH 9.0 the reaction is over within two minutes using the vinyl sulfone and within 15 minutes using the chloroethyl sulfone. However, these reactions were too fast for determination of accurate rate constants. At pH 8.0 the reactions were slower, but still complete in one hour for vinyl sulfone and in three hours for the chloroethyl sulfone. The conversion of chloroethyl sulfone to vinyl sulfone is significantly slower than the reaction of vinyl sulfone with Cys—SH. Thus the rate of reaction for chloroethyl sulfone with Cys—SH appears to be dependent on the rate of conversion of chloroethyl sulfone to vinyl sulfone. Nevertheless, these reaction rates were still much faster than for the reaction with Lys—NH$_2$.

The above kinetic studies demonstrate the following points. PEG vinyl sulfone is much more reactive with thiol groups than with amino groups, indicating that attachment of PEG vinyl sulfone to a protein containing both cysteine and lysine groups proceeds primarily by reaction with cysteine. Since reactivity with amino groups is similar to imino groups, then reactivity of histidine subunits will also be much lower than reactivity with cysteine subunits. Also, selectivity toward thiol groups is accentuated at lower pH values for PEG chloroethyl sulfone and PEG vinyl sulfone, although the reactions of PEG chloroethyl sulfone are somewhat slower.

The utility of many PEG derivatives is limited because they react rapidly with water, thus interfering with attempts to attach the derivative to molecules and surfaces under aqueous conditions. The following Example 3 shows that PEG vinyl sulfone and PEG chloroethyl sulfone are stable in water.

EXAMPLE 3

Hydrolytic Stability

PEG vinyl sulfone was dissolved in heavy water, D$_2$O deuterium oxide, and monitored by NMR. Reaction did not occur. A solution of PEG chloroethyl sulfone produced PEG vinyl sulfone in heavy water that was buffered with borate to pH 9.0. Monitoring with NMR showed that PEG vinyl sulfone, once produced, was stable for three days in heavy water.

PEG chloroethyl sulfone is stable in water until solution becomes basic, at which time it is converted into vinyl sulfone. Conversion to vinyl sulfone has been demonstrated by dissolving PEG chloroethyl sulfone in water at pH 7 and in borate buffer at pH 9. The PEG derivative is extracted into methylene chloride. Removal of methylene chloride followed by NMR analysis showed that PEG chloroethyl sulfone is stable at a neutral pH of 7.0, and reacts with base to produce PEG vinyl sulfone.

Vinyl sulfone is stable for several days in water, even at basic pH. Extensive hydrolytic stability and thiol-specific reactivity of PEG vinyl sulfone means that PEG vinyl sulfone and its precursor are useful for modification of molecules and surfaces under aqueous conditions, as shown in the following Example 4.

EXAMPLE 4

Conjugation to BSA

Protein modification was demonstrated by attachment of the PEG derivative to bovine serum albumin (BSA) by two different methods. BSA is a protein. Native unmodified BSA contains cystine groups which do not contain thiol groups. The cystine units are tied up as disulfide linkages, S—S.

In the first method, m-PEG (monomethoxy-PEG) vinyl sulfone of molecular weight 5,000 was reacted with unmodified BSA for 24 hours in a 0.1 M borate buffer at pH 9.5 at room temperature. The solution contained 1 mg of BSA and 1 mg of m-PEG vinyl sulfone, of molecular weight 5,000, per mL of solution. The results from the Example 2 model compounds had indicated that lysine subunits (and possibly histidine subunits) would be modified under these relatively basic conditions and in the absence of free thiol groups available for reaction.

Attachment to lysine subunits was demonstrated in two ways. First, size exclusion chromatography showed that the molecular weight of the protein had increased by approximately 50%, thus indicating attachment of approximately 10 PEGs to the protein. Second, fluorescamine analysis showed that the number of lysine groups in the BSA molecule had been reduced by approximately ten.

In the second method, the BSA was treated with tributylphosphine to reduce the disulfide S—S bonds to thiol groups, —SH, which are available for reaction. The modified BSA was then treated with PEG chloroethyl sulfone at pH 8.0 in a 0.1 M phosphate buffer at room temperature for 1 hour. The solution contained 1 mg of modified BSA and 1 mg of m-PEG chloroethyl sulfone of molecular weight 5,000 per mL of solution. The results showed that lysine groups were unreactive under these conditions. However, thiol groups were reactive.

Attachment of the PEG to the protein was demonstrated by size exclusion chromatography, which showed an increase in the molecular weight of the protein by about 25%. Fluorescamine analysis indicated no change in number of lysine subunits in the protein, thus confirming that PEG attachment did not take place on lysine subunits. Substitution on thiol groups was thereby confirmed.

EXAMPLE 5

Synthesis of Vinyl Sulfone NHS-ester Heterobifunctional PEG (3,400) Reagent

Briefly, PEG(3,400)-ω-vinyl sulfone-α-priopionic acid, succinimidyl ester was synthesized in several steps. First, the ethyl ester of PEG(3,400)-ω-hydroxy-α-propionic acid was synthesized. Second, the ethyl ester was converted to the ω-mesylate derivative. Third, the mesylate was used to prepare the ω-thioethanol derivative. Fourth, the thioethanol derivative was converted to the ω-hydroxysulfone. Fifth, the hyroxysulfone was converted to the ω-vinyl sulfone. The latter α-ethyl ester was converted to the α-propionic acid in a sixth step. Finally, the propionic acid group was converted to the succinimidyl ester. The detailed synthesis is set forth below.

Step 1. 15.0 grams of PEG(3,400)-ω-hydroxy-α-propionic acid, 75 mL anyhydrous ethyl alcohol, and 3 mL sulfuric acid were heated to reflux for 1 hour. After cooling to room temperature, 50 mL water was added to the reaction mixture and sodium bicarbonate was used to adjust pH to 7. Ethyl alcohol was distilled off under reduced pressure using a rotoevaporator at 55° C. for one-half hour. The reaction product was extracted with 60, 50 and 40 mL dichloromethane. The extract was dried with anhydrous magnesium sulfate, concentrated to 50 mL, and added to 400 mL cold diethyl ether. The precipitated product was filtered off and dried under reduced pressure. The yield of the ethyl ester was 13.1 grams. NMR analysis showed 49% propionic acid, ethyl ester groups and 51% PEG—OH groups.

Step 2. A mixture of 13.0 grams (0.0038 mol) of the ethyl ester derivative formed in step 1, 100 mL toluene, and 2.0 grams BHT was azeotropically dried during heating to reflux. Next, 15 mL dry dichloromethane, 0.60 mL (0.0043 mol, 1.15 fold excess) triethylamine and 0.31 mL (0.0040 mol, 1.07 fold excess) mesyl chloride were added at 5° C. and the mixture was stirred overnight at room temperature under a nitrogen atmosphere. 2 mL anhydrous ethyl alcohol was added and the mixture was stirred for 15 minutes. The mixture was then filtered and about 70 mL of solvents were distilled off under reduced pressure to yield a toluene solution of PEG-ω-mesylate-α-propionic acid ethyl ester.

Step 3. The following were added to about 40 mL (0.00375 mol) of the PEG-ω-mesylate-α-propionic acid ethyl ester solution obtained in step 2: 150 mL of anyhydrous ethyl alcohol, 1.79 mL (0.0139 mol, 3.69 fold excess) mercaptoethanol and 0.45 grams (0.0011 mol, 3.0 fold excess) sodium hydroxide dissolved in 20 mL anhydrous ethyl alcohol. The mixture was heated 3 hours at 58–62° C. under a nitrogen atmosphere. After cooling to room temperature, acetic acid was used to adjust the pH to about 6.5 and 140 mL of ethyl alcohol was distilled off under reduced pressure using a rotoevaporator, at 55° C. for 40 minutes. After distillation, 50 mL dichloromethane was added to the residue. The resulting solution was washed with distilled water and dried with anhydrous magnesium sulfate. The solution was then concentrated to 30 mL and added to 350 mL cold diethyl ether. The precipitated product was filtered off and dried under reduced pressure. The yield of the thioethanol derivative was 11.5 grams. NMR analysis showed 52% thioethanol groups, 35% propionic acid, ethyl ester groups and 13% PEG—OH moieties.

Step 4. Next, a solution of 11.5 grams PEG-ω-thioethanol-α-propionic acid, ethyl ester in 12 mL distilled water was prepared. A tungstic acid solution was also prepared as follows: 0.14 grams of tungstic acid, 12.0 mL distilled water and 0.05 grams sodium hydroxide dissolved in 6.0 mL water were mixed to form a solution having a pH of 11.5. A 10% solution of $NaH_2PO_4$ was added to the tungstic acid solution to adjust the pH to 6.6. The 12 mL solution of ethyl ester was then added to the pH 6.6 tungstic acid solution and the pH was again adjusted to 6.6 with 0.1M NaOH. 1.1 mL of 30% hydrogen peroxide was added and the reaction mixture was stirred for 19 hours. The pH after the reaction period was 6.7. 1M NaOH was added to adjust the pH to 7.2 and the reaction mixture was stirred for 1 hour. 5 grams of sodium chloride dissolved in 45 mL distilled water was added to the reaction mixture. The reaction product was extracted 3 times with 50 mL dichloromethane. The extract was dried with magnesium sulfate as follows: 10 grams powdered magnesium sulfate was added to the extract and the magnesium sulfate was filtered away after two hours. The magnesium sulfate dried extract was concentrated to 40 mL and added to 350 mL cold diethyl ether. The precipitated product was filtered off and dried under reduced pressure.

The yield was 9.7 grams and contained 50% hydroxysulfone groups, 39% propionic acid, ethyl ester groups and 11% PEG—OH groups as determined by NMR.

Step 5. To a mixture of: 9.6 grams (0.00271 mol) of the PEG-ω-hydroxysulfone-α-propionic acid, ethyl ester synthesized in step 4, 50 mL dichloromethane and 0.01 grams (0.1 wt % per PEG) BHT stirred at room temperature under a nitrogen atmosphere was added 3.00 mL (0.0215 mol, 3.97 fold excess) triethylamine and 0.80 mL (0.010 mol, 3.81 fold excess) mesyl chloride. The reaction mixture was stirred for 15 minutes, filtered, and diluted with 150 mL dichloromethane. The resulting mixture was then washed with 25 mL 1M HCl, 25 mL 10% NaCl and 25 mL water. A small amount of $Na_2HPO_4$ was added to adjust the pH of the water layer to 7. The reaction mixture was then dried with magnesium sulfate and concentrated to 40 mL. The obtained solution was added to 400 mL cold diethyl ether. The precipitated product was filtered off and dried under reduced pressure to yield 9.1 grams. NMR analysis showed the following functionalities: 43% vinyl sulfone, 16% mesylate, and 35% propionic acid, ethyl ester.

Step 6. To a solution of 9.0 grams of the PEG-ω-vinyl sulfone-a propionic acid, ethyl ester derivative in 50 mL distilled water, 1.0M NaOH was added to adjust the pH to 12.0 and the solution was stirred 1.5 hours keeping the pH between 11.9 and 12.1 by periodic addition of 1.0M NaOH. Next, the pH was adjusted to 3.0 with oxalic acid, 5 grams of NaCl was added to the solution, and the reaction product was extracted 3 times with 50 mL dichloromethane. The extract was dried with anhydrous magnesium sulfate, concentrated to 30 mL and added to 350 mL cold diethyl ether.

The precipitate was filtered off and dried under reduced pressure. The yield was 6.8 grams. Functional groups identified by NMR analysis were: vinyl sulfone 40%, propionic acid 29%, propionic acid, ethyl ester 4%, and 17% mesylate. The precipitate was purified by ion-exchange chromatography over a DEAE Sepharose FF column. The yield after purification was 3.2 grams and NMR analysis showed 50% propionic acid groups, 38% vinyl sulfone groups, and 8% mesylate groups.

Step 7. A mixture of 3.0 grams PEG-ω-vinyl sulfone-α-propionic acid, 0.12 grams N-hydroxysuccinimide, 0.21 grams DCC (dicyclohexylcarbodiimide) in 20 mL dichloromethane was stirred overnight at room temperature under a nitrogen atmosphere. The reaction mixture was then filtered and added to 250 mL cold diethyl ether. The precipitated product was filtered off and dried under reduced pressure to yield 2.90 grams. NMR showed the following groups: succinimide 50%, 38% vinyl sulfone, 10% mesylate, and 2% hydroxysulfone.

EXAMPLE 6

Synthesis of Maleimide, NHS-ester Heterobifunctional PEG (3,400) Reagent

The maleimide, NHS-ester PEG reagent was synthesized in two steps. In the first step, maleimido-PEG—OH was synthesized. Specifically, 0.130 grams maleimido succinimidyl propionate were dissolved in 5 mL dry dichloromethane and cooled to 0° C. Next, 0.5 grams PEG-monoamine, prepared as described below, was added and then 2 drops of triethylamine. After 2 hours at room temperature, TLC indicated that the reaction was complete. TLC was conducted using n-BUOH—ACOH—$H_2O$ at a ratio of 4:1:1. The reaction mixture was evaporated to dryness and the residue dissolved in 15 mL distilled water. The pH of the solution was adjusted to 3 using 15 mL 0.5M HCl and extracted with 10 mL $CH_2Cl_2$. The organic layer was dried with magnesium sulfate, filtered, concentrated to 15 mL, and poured into 75 mL cold ether. The precipitate was filtered and dried in vacuo. The yield was 0.300 grams. NMR analysis showed 77% maleimide groups and 100% PEG—OH.

In the second step, the maleimido-PEG—OH was converted to the maleimide-PEG—NHS-ester. A mixture of 2 mL $CH_2Cl_2$, 0.05 mL pyridine (1 equivalent) 1 mL acetonitrile and 0.266 grams maleimido-PEG—OH was stirred at room temperature under nitrogen. To this mixture, 0.070 grams (2.5 equivalents) N,N-disuccinimidyl carbonate was added and the reaction left overnight. The reaction mixture was then poured into approximately 50 mL cold ether, filtered and dried in vacuo. The NMR showed impurities and the product was precipitated a second time with a final yield of 0.230 grams.

The PEG-monoamine used in the first step above was prepared in three steps as follows. First, the PEG-mesylate derivative was formed. From the mesylate, the amine was formed. Finally, the monoamine was separated from the underivatized PEG and the diamine.

Step 1 PEG-3,400 (120 grams, 0.07164 equivalents of OH) was dissolved in 580 mL toluene, azeotropically dried, and then 90 mL dichloromethane, 1.80 mL triethylamine (0.01291 mol) and 0.83 mL mesyl chloride (0.01072 mol) were added. After overnight reaction at room temperature, 90 mL of solvents were distilled off from the reaction mixture under reduced pressure, the mixture was filtered and then 500 mL toluene was distilled off under reduced pressure. The residue was added to 800 mL cold diethyl ether. The precipitated product was filtered off and dried under reduced pressure. The yield was 118 grams and the substitution was 15%.

Step 2 118 grams of the mesylate formed in step 1 and 80 grams ammonium chloride were dissolved in 1600 mL concentrated aqueous $NH_4OH$ and stirred at room temperature for 44 hours. The reaction product was extracted with 600, 400, and then 200 mL dichloromethane. The extract was washed with 170 mL 2% KOH and 170 mL water, dried with magnesium sulfate, concentrated to 200 mL and added to 800 mL cold diethyl ether. The precipitated product was filtered off and dried under reduced pressure. The yield was 106 grams and the substitution was 15.6%.

Step 3 45 grams of the amine formed in step 2 was dissolved in 9 L water and loaded onto SP-Sepharose FF (300 mL of gel equilibrated with 1000 mL citric acid-lithium citrate buffer, 0.4%, pH 3.0, and then washed with water). SP-Sepharose FF is available from Pharmacia, Uppsala, Sweden. The underivatized PEG was washed off the column with water. Next, PEG monoamine was eluted with 800 mL 20 mM NaCl. The pH of the eluate was adjusted to 11 with 1M NaOH and the PEG monoamine was extracted with dichloromethane, dried with magnesium sulfate, and the solvent was distilled off. The yield was 9 grams.

EXAMPLE 7

SYNTHESIS OF PEG-α,ω-bis-vinyl Sulfone

The synthesis of 3,400 and 20,000 kDa PEG bis-vinyl sulfone was conducted using PEG diol and the general method set forth above. PEG diol was purchased from Fluka Chemical Corporation (Ronkonkoma, New York) or from Nippon Oil and Fat (Tokyo, Japan).

EXAMPLE 8

PEGYLATION of IL-1ra Using PEG-20,000-α,ω-bis-vinyl Sulfone

The IL-1ra c84 mutein was prepared as set forth in published PCT Application WO 92/16221, incorporated herein by reference. Conjugation of the c84 mutein or the native (wild-type) IL-1ra using PEG-α,ω-bis-vinyl sulfone (3,400 or 20,000 kDa) was conducted at 25° C. in citrate buffer, pH 6.75–7.5, in 1 mL tubes, varying PEG and protein concentrations. At a protein concentration of 30 mg/mL, good conversion to the dumbbell molecule was obtained within 18 hours. At a protein concentration of 0.94 mg/mL, mostly monoadducts were obtained. The dumbbell species was preferentially formed at a protein concentration of 100 mg/mL with 0.03 equivalents PEG. The dumbbell can be purified using chromatographic techniques set forth in PCT Publication Publication No. WO 92/16221, incorporated herein by reference.

In other experiments 0.1 M Tris-HCl buffer, pH 8.5, containing 30 mg/mL of the wild-type IL-1ra was treated with a 0.53 molar equivalent of the 20 kDa PEG-bis-vinyl sulfone at 25° C. for 18 hours. SDS PAGE analysis showed conversion to both dumbbell and the monoadduct. At a protein concentration of 3.1 mg/mL with 1 molar equivalent of PEG reagent, only the monoadduct was observed.

In general, the c84 mutein reacts more readily with the PEG reagent than the wild-type molecule.

EXAMPLE 9

Bioactivity of IL-1ra Dumbbell

The c84 dumbbell generated above was analyzed for its receptor binding affinity compared to that of unPEGylated recombinant IL-1ra on murine EL-4 cells using the assay set forth in PCT Application Publication No. WO 92/16221, incorporated herein by reference. The results showed similar binding affinities between the two molecules.

EXAMPLE 10

PEGYLATION of TNFbp c105 Mutein with PEG-20,000-α,ω-bis-vinyl Sulfone

The c105 mutein of TNFbp was prepared as set forth in published PCT Publication WO 92/16221, incorporated herein by reference. Alternatively, the c105 mutein was prepared as follows. E. Coli cells expressing the c105 mutein were harvested by centifugation. The cell sludge was adjusted to approximately 40% wet weight solids by the addition of purified water. The mixture was then further diluted with an equal volume of breaking buffer (50 mM Tromethamine, 4 mM EDTA, pH 7.2) to give a suspension with approximately 20% wet weight solids. The cell sludge was passed five times through a high pressure homogenizer operating at approximately 8,000 psi to produce the cell homogenate. The homogenate was cooled to less than or equal to 10° C. prior to each pass through the homogenizer. The homogenate was centrifuged and the solids fraction containing the c105 was retained. The solids were diluted and centrifuged again to give washed inclusion bodies.

The washed inclusion bodies were then dissolved by addition of 8 M urea and 150 mM cysteine in 50 mM TRIS, pH 9.5 This mixture was allowed to stir for two hours at room temperature prior to refolding. Under these conditions, the c105 mutein was denatured and reduced.

The reduced denatured c105 mutein was refolded by dilution with 1.1 M urea, 50 mM Tris to give a final refold solution comprised of 200 ug/mL c105 mutein, 1.5 M urea, 7.5 mM cysteine, 50 mM Tris, pH 9.7. The refold mixture was held at 6–1° C. for two days. Refold efficiency was monitored by reverse phase HPLC and cation exchange HPLC.

The refold mixture was then brought to pH 5.0 by addition of acetic acid and HCl. The refold mixture was loaded onto a cation exchange column (S-Sepharose big bead resin) previously equilibrated in 25 mM sodium acetate, 65 mM NaCl, pH 5 at 4° C. After loading, the column was washed with the same equilibration buffer. The column was eluted with a gradient from 65 to 350 mM NaCl in 25 mM sodium acetate, pH 5. The c105 mutein eluted at about 200 mM NaCl and was collected in one pool.

The collected pool containing the c105 mutein was diluted with 1.5 volumes of 5 M NaCl, 40 mM sodium phosphate, adjusted to pH 6, and loaded onto a hydrophobic interaction column (Toyo Butyl 650 M column), previously equilibrated in 3 M NaCl, 20 mM sodium phosphate, pH 6. At the end of the load, the column was washed with equilibration buffer. The c105 mutein was eluted using a linear eight column volume decreasing salt gradient running from 3 M to 1 M NaCl, in 20 mM sodium phosphate, at pH 6. The c105 mutein was collected in one pool. The pool was then concentrated to approximately 3 g/L c105 mutein and then diafilted against 20 mM sodium phosphate, pH 6.0 until the final conductivity was less than 4 mmho (approximately six volumes).

The diafiltered pool was loaded onto a SP-Sepharose high performance column equilibrated in 20 mM sodium phosphate, pH 6.0. After loading, the column was washed with additional equilibration buffer and eluted with a combination pH/salt gradient from 20 mM sodium phosphate, 50 mM NaCl, pH 6.0 to 20 mM sodium phosphate, 50 mM NaCl, pH 6.5. The c105 mutein eluted in the later half of the gradient at about 35 mM NaCl. The c105 mutein can be stored frozen at this point.

The c105 mutein was reacted with the PEGylation reagent at molar ratios of PEG reagent to protein of 1:1, 2:1, 4:1, 1:2 and 0:1 (control). The reaction was carried out in 20 mM phosphate/20 mM acetate buffer at pH 7.5 for 15 hours at 22° C. Reactions were also carried out in 50 mM phosphate buffer, pH 7.5 or 8.5.

The percent conversion to the dumbbell molecule was determined by cation exchange HPLC over a MA7S column. The percent conversion ranged from approximately 40–60%. Conversion to the dumbbell molecule was optimized by adding a solution of approximately 50 mg/mL of PEG reagent to the protein at a molar ratio of 0.50–0.65 PEG reagent to 1.0 of TNFbp mutein at pH 7.5 for 15 hours at 22° C. As the ratio of PEG to protein is increased, production of the monoadduct was favored. Monoadduct formation was optimized by a 5:1 ratio of PEG reagent to protein.

Conjugates were purified by chromatography over an S-Sepharose HP column. The reaction mixture was adjusted to pH 3.0–4.2 and loaded onto the column previously adjusted to the same pH. The column was washed with an equilibration buffer and the dumbbell was eluted using a liner sodium chloride gradient and a flow rate of 1.2–1.5 cm/min. The following species eluted from the column in the following order: 1) monosubstituted, 2) dumbbell, 3) unPEGylated TNFbp mutein, and 4) aggregated mutein.

EXAMPLE 11

Bioactivity of TNFbp c105 Mutein Dumbbell c105 dumbbells, whether formed from PEG-bis maleimide as described in PCT Application Publication No. WO 92/16221 or as described herein, were shown to be 50 to 100 fold more active than the unPEGylated 30 kDa TNF inhibitor by comparison in the L929 cytotoxicity assay set forth in WO 92/16221, incorporated herein by reference.

EXAMPLE 12

Preparation of Glyceryl-PEG-tris-vinyl Sulfone

Glyceryl-PEG-α,β,γ-triol (10,000 kDa and 20,000 kDa) was converted to the vinyl sulfone derivative using the general method described above. Glyceryl-PEG-α,β,γ-triol was purchased from Union Carbide, Terrytown, N.Y. Glyceryl-PEG-α,β,γ-triol can be synthesized by ethylene oxide polymerization off of glycerol in base.

EXAMPLE 13

Synthesis of TNFbp c105 Trumbbell Using Glyceryl-PEG-tris-vinyl Sulfone

Three TNFbp c105 muteins were conjugated to PEG-tris-vinyl sulfone to yield a "trumbbell" molecule. Experiments conducted over a wide range of PEG:protein ratios showed that a particularly useful molar ratio for conversion to the trumbbell was 0.25–0.35 PEG to 1 protein. In a typical experiment, the c105 mutein in 20 mM phosphate, 20 mM acetate buffer, pH 7.5 was exposed to a 0.03 molar equivalent of glyceryl-PEG-10,000-α, β, γ-triol at 25° C. for 18 hours. Analysis of the latter reaction mixture by cation exchange HPLC (Bio Rad MA7S column eluting a sodium chloride gradient) indicated conversion to the trumbbell in 49% yield and bi-substitution in a 34.9% yield.

EXAMPLE 14

Synthesis of IL-1ra Trumbell Using Glyceryl-PEG-tris-vinyl Sulfone

A solution of PEG-10,000-$\alpha,\beta,\gamma$-tris-vinyl sulfone was reacted with 20 mg/mL wild-type IL-1ra in 0.1 M phosphate buffer at the following PEG/protein molar ratios: 0.10:1; 0.25:1; 0.35:1; 0.45:1; 0.55:1; 0.65:1. The reactions were incubated at 25° C. for 72 hours. SDS PAGE analysis showed conversion to mono, di, and triadducted products. Optimal conversion to the triadduct was observed at a PEG/protein ratio of 0.10:1. The reaction mixture was applied to an S Sepharose high performance column and eluted with a sodium chloride gradient.

EXAMPLE 15

Synthesis of c105 TNFbp-PEG-IL-1ra Heterodumbbell

A solution of wild-type IL-1ra in 0.1 M phosphate buffer, pH 8.5 was reacted with 8 mg/mL PEG-20,000-bis-vinyl sulfone-mono-c105TNFbp adduct at the following molar ratios and concentrations of IL-1ra indicated: 55:1 (12.5 mg/mL); 85:1 (18.75 mg/mL); 100:1 (25.0 mg/mL) and 150:1 (31.75 mg/mL). After 72 hours, heterodumbbell was formed as determined by SDS PAGE. Optimal conversion was observed at a ratio of 1:100 monoadduct to IL-1ra. The heterodumbbell was purified using an S Sepharose high performance column and eluting with a sodium chloride gradient.

EXAMPLE 16

Stability of PEG-vinyl Sulfone Polypeptide Adducts

The stability of the linkage between the c105 TNFbp mutein and PEG-bis-vinyl sulfone was studied. Known amounts of the c105 dumbbell were incubated in PBS, pH7.4, at 37° C. for up to one week with aliquots removed at intervals for analysis by SDS PAGE. Essentially no decomposition of the c105 dumbbell was observed. At pH 10 at 37° C. for 1 week, only 5–10% degradation of the conjugate was observed.

EXAMPLE 17

TNFbp c105 Dumbbell Inhibits Actively-induced Experimental Allergic Encephalomyelitis ("EAE")

The in vivo activity of the c105 dumbbell made with PEG-bis-vinyl sulfone has been demonstrated. EAE is a murine model of an autoimmune inflammatory demyelinating disease of the central nervous system that is often used as a model for human MS. AS described below, the c105 dumbbell inhibited EAE in rats.

Female Lewis rats (150–200 g) were purchased from Charles River (Raleigh, N.C.), and housed for at least 1 week before starting experiments. They received food and water ad libitum and were housed in temperature and light controlled (12 h/day) rooms. Within each experiment, animals were age-matched.

Active induction of EAE Rats (usually six per group) were anesthetized with 2% isoflurane+$O_2$ and immunized on day 0 in the footpad of the left hind limb with 0.1 mL of an emulsion containing myelin basic protein ("MBP") at one of the following doses; 0, 1, 3, 10 or 30 $\mu$g (fragment 68–84 Bachem Bioscience, PA). The MBP was dissolved in phosphate buffered saline (PBS) and emulsified with an equal volume of complete Freund's adjuvant (CFA) containing 5 mg/mL of *Mycobacterium tuberculosis* H37Ra (Difco Lab, Mich.). Control rats received 0.1 mL of the PBS/CFA emulsion with no MBP in the footpad of the left hindlimb.

Clinical Scoring of EAE Evaluation of clinical disease was performed on a daily basis using a standard 0–5 scoring system. Briefly, the spectrum of rating was 0 normal, 0.5 partial loss of tail tone, 1 complete loss of tail tone, 2 dragging of one hind limb, 3 paralysis of both hind limbs, 4 morbid, and 5 death. Daily weights were recorded for individual rats and weight loss/gain was expressed relative to initial weight.

Effects of immunization with MBP Initial studies assessed the clinical severity of different doses of MBP (0.1–30 $\mu$g/0.1 mL) in the emulsion described above in the rat. The 0.1 and 0.3 $\mu$g MBP doses produced no apparent clinical signs. The 30 ug dose of MBP produced the most severe clinical signs, compared to the 1 ug dose. This effect was highly significant ($p<0.001$, Mann-Whitney U-test). In general increasing the dose (1–30 $\mu$g) of MBP produced clinical signs earlier, for example 1ug MBP had a mean±S.E.M. onset of 14.88±0.42 (n=9) compared to 12.35±0.16 (n=34; $p<0.01$) days for the 30 ug MBP dose. In addition, a dose dependent effect of MBP (1–30 ug) on weight loss was observed. Animals spontaneously recovered from the clinical signs within 5–7 days of onset. Administration of CFA alone produced no clinical signs, however, there was an initial transient weight loss compared to non-treated controls.

In all of these studies no significant differences at any of the MBP doses were observed between the no drug (MBP immunized only) and vehicle dosed groups (MBP immunized and dosed with PBS). Thus, vehicle had no effect on the severity of the disease (see Tables 3 and 4). The no drug and vehicle dosed groups are described below.

Treatment of EAE Various doses of TNF inhibitor dumbbell (0.1–3 mg/kg) or vehicle (PBS) at various time courses were administered by subcutaneous injection. Treatment periods began either immediately after or nine days after immunization with MBP and continuing until 21 days post immunization. In each experiment, the control rats receiving PBS received the same number of injections as the treatment groups to diminish any secondary effects due to stress. A group of rats receiving no injections whatsoever after EAE induction, the no drug control, was also observed.

Effects of treatment Every day dosing The effects on EAE of everyday dosing with the TNF inhibitor dumbbell, starting on the day of immunization for a total of 21 days, was evaluated. Dumbbell concentrations of 0.1, 0.3, 1 or 3 mg/kg had no significant effects on reducing severity of the clinical signs in the 1 ug and 30 ug MBP groups. However, significant amelioration of the clinical disease was observed at the 3 ug MBP dose for all dumbbell doses used.

Every other day dosing The effects of 0.1, 0.3, 1 and 3 mg/kg doses given every other day starting on day nine post immunization were also tested. As shown in Tables 3 and 4, a significant inhibition of clinical signs occurred at doses of 0.3 ($p<0.008$), 1.0 ($p<0.001$) and 3.0 mg/kg ($p<0.002$, Mann Whitney test, n=6) compared to vehicle controls using the highest MBP dose (30 ug/0.1 mL). No significant differences between the vehicle and the no treatment control groups were observed. The lowest dose of the TNF inhibitor dumbbell had no significant effect on clinical signs.

Dumbbell doses of 1.0 ($p<0.1$) and 3 mg/kg ($p<0.05$, Mann Whitney test) significantly attenuated the clinical signs produced by 10 ug MBP. Although 0.3 and 0.1 mg/kg dumbbell attenuated the clinical signs the reduction was not significant. Dumbbell doses of 0.1–3 mg/kg did not significantly inhibit the clinical signs induced by lower doses of MBP (1 or 3 ug).

Weight loss is an important marker of EAE onset. Rats immunized with 3, 10, and 30 ug MEBP that received the c105 dumbbell (1 or 3 mg/kg) lost less weight compared to the vehicle groups.

TABLE 3A

| Treatment | no drug | | | | | | |
|---|---|---|---|---|---|---|---|
| Mean | 0.25 | 1.00 | 1.92 | 2.67 | 1.83 | 0.83 | 0.166 |
| Clinical | ± | ± | ± | ± | ± | ± | ± |
| Score | 0.18 | 0.50 | 0.52 | 0.44 | 0.53 | 0.44 | 0.10 |
| Days | 11 | 12 | 13 | 14 | 15 | 16 | 17 |

TABLE 3B

| Treatment | vehicle | | | | | | |
|---|---|---|---|---|---|---|---|
| Mean | 0.17 | 0.75 | 1.83 | 2.50 | 2.08 | 1.00 | 0.25 |
| Clinical | ± | ± | ± | ± | ± | ± | ± |
| Score | 0.17 | 0.31 | 0.40 | 0.34 | 0.45 | 0.41 | 0.11 |
| Days | 11 | 12 | 13 | 14 | 15 | 16 | 17 |

TABLE 3C

| Treatment | 0.1 mg/kg dumbbell | | | | | | |
|---|---|---|---|---|---|---|---|
| Mean | 0.08 | 0.92 | 1.33 | 2.67 | 2.17 | 1.17 | 0.25 |
| Clinical | ± | ± | ± | ± | ± | ± | ± |
| Score | 0.08 | 0.35 | 0.21 | 0.21 | 0.30 | 0.28 | 0.11 |
| Days | 11 | 12 | 13 | 14 | 15 | 16 | 17 |

TABLE 3D

| Treatment | 0.3 mg/kg dumbbell | | | | | |
|---|---|---|---|---|---|---|
| Mean | 0.25 | 0.92 | 1.50 | 1.17 | 0.58 | 0.375 |
| Clinical | ± | ± | ± | ± | ± | ± |
| Score | 0.17 | 0.27 | 0.42 | 0.40 | 0.15 | 0.14 |
| Days | 12 | 13 | 14 | 15 | 16 | 17 |

TABLE 3E

| Treatment | 1 mg/kg dumbbell | | | | | |
|---|---|---|---|---|---|---|
| Mean | 0.17 | 0.58 | 0.67 | 0.42 | 0.33 | 0.083 |
| Clinical | ± | ± | ± | ± | ± | ± |
| Score | 0.17 | 0.20 | 0.17 | 0.20 | 0.17 | 0.083 |
| Days | 12 | 13 | 14 | 15 | 16 | 17 |

TABLE 3F

| Treatment | 3 mg/kg dumbbell | | | | | |
|---|---|---|---|---|---|---|
| Mean | 0.25 | 0.42 | 0.83 | 0.42 | 0.08 | 0.08 |
| Clinical | ± | ± | ± | ± | ± | ± |
| Score | 0.17 | 0.20 | 0.25 | 0.32 | 0.08 | 0.08 |
| Days | 12 | 13 | 14 | 15 | 16 | 17 | table legend: Daily mean severity score in rats immunized with 30 ug MBP and treated with TNF inhibitor dumbbell every other day starting 9 days post MBP-immunization. Vehicle group received PBS and the no drug group received no injections post EAE induction.

TABLE 4

INHIBITORY EFFECTS OF TNF INHIBITOR DUMBBELL EXPRESSED AS AREA UNDER CURVE

| Treatment | no drug | vehicle | 0.1 mg/kg | 0.3 mg/kg | 1 mg/kg | 3 mg/kg |
|---|---|---|---|---|---|---|
| Clinical Severity (Area) | 8.07 ± 1.40 | 7.83 ± 0.88 | 7.88 ± 0.83 | 4.3 ± 1.02 | 1.63 ± 0.60 | 1.53 ± 1.01 | table legend:
Inhibitory effects of c105 dumbbell of clinical severity expressed as area under curve (units arbitrary).
Mean ± S.E.M.
(n = 6) were determined for each group and compared statistically against the vehicle group (Mann-Whitney test). No significant differences between the vehicle and no drug control group were observed. c105 dumbbell at 0.3, 1.0 and 3.0 mg/kg (given as described above) significantly (**p < 0.008, 0.001, and 0.002 respectively) reduced clinical signs.

TABLE 5

DURATION OF THE DISEASE WITH EVERY OTHER DAY DOSING

| | TNF inhibitor dumbbell mg/kg | | | | |
|---|---|---|---|---|---|
| MBP μg | 0 | 0.1 | 0.3 | 1 | 3 |
| 30 | 5.33 ± 0.21 | 5.50 ± 0.34 | 4.50 ± 0.92 | 2.83 ± 0.79* | 2.16 ± 0.60** |
| 10 | 4.33 ± 0.80 | 3.66 ± 0.80 | 4.00 ± 0.51 | 3.33 ± 0.49 | 1.83 ± 0.70* |
| 3 | 2.50 ± 1.02 | 1.83 ± 0.83 | 2.00 ± 0.81 | 3.16 ± 0.74 | 0.83 ± 0.54 |
| 1 | 1.83 ± 0.79 | 0.66 ± 0.66 | 1.66 ± 0.61 | 1.33 ± 0.49 | 0.66 ± 0.42 |

*p < 0.05
**p < 0.01

Single dosing A single dose of either 0.3 or 3 mg/kg dumbbell administered on day nine post immunization had little or no effect on attenuating MBP (1–30 μg) induced clinical signs when compared to vehicle controls.

Every third day administration of TNF inhibitor dumbbell Dumbbell at 0.1–3 mg/kg or vehicle was administered on days 9, 12, 15 and 18 post MBP-immunization. As shown in Table 6, a significant attenuation of MBP (30 μg) induced clinical signs was observed at c105 dumbbell doses of 0.3 (p<0.05), 1.0 (p<0.01) and 3 mg/kg (p<0.001 Mann- Whitney t-test). The 0.1 mg/kg dose of c105 dumbbell was without effect when compared to the vehicle control.

The MBP (10 μg) induced clinical signs were reduced by 0.3, 1.0 and 3.0 mg/kg c105 dumbbell doses. However, significant (p<0.05 and 0.03 respectively) effects were only observed at the higher c105 dumbbell doses. Although c105 dumbbell (0.3–3 mg/kg) reduced the clinical signs produced by 3 ug of MBP by approximately 20–60%, the effects observed were not significantly different from the vehicle control group.

The duration of the disease was generally reduced by c105 dumbbell. For example, c105 dumbbell at 1 and 3 mg/kg significantly reduced the duration MBP (30 μg) mediated signs by 37.3% and 68.7% respectively (see Table 10). A similar trend was also observed using the intermediate MBP (10 g) dose but not the lowest MBP dose (Table 7).

Disease onset in the 10 and 30 μg MBP groups were significantly (p<0.047; p<0.013 respectively; Mann Whitney U-test) delayed in those animals that were treated with 3 mg/kg c105 dumbbell.

The weight loss associated with EAE was partially inhibited by c105 dumbbell especially at the 1 and 3 mg/kg doses. The reduction in weight loss was dose dependent. This effect of c105 dumbbell was similar no matter what dose of MBP was used.

TABLE 6

MEAN CLINICAL SEVERITY EXPRESSED AS AREA FOR EVERY THIRD DAY DOSING

| Treatment | Vehicle | 0.1 mg/kg | 03. mg/kg | 1.0 mg/kg | 3.0 mg/kg |
|---|---|---|---|---|---|
| Mean Clinical Severity (Area) | 9.21 ± 0.64 | 8.25 ± 0.92 | 6.23 ± 1.37 | 3.66 ± 0.61 | 0.33 ± 0.17 | chiasm caudal to the attachment of the pituitary and the transverse fibers of the pons. The spinal cord was trimmed by maling 4–6 cross sections through the cervical, thoracic and lumber portions. The sacral segment with attached caudal nerves was embedded longitudinally. Tissues were processed for paraffin embedding and stained with hematoxylin and eosin.

Histologic evaluations were done without knowledge of the treatment groups. Each slide was assigned a numerical score ranging from 1–4 to indicate the intensity of inflammation and demyelination. Scoring criteria were as follows; 1=minimal 1–2 vessels have small perivascular cuffs of inflammatory cells, 2=mild 3 or more vessels have small perivascular cuffs of inflammatory cells with little if any extension of inflammation into parenchyma, 3=moderate 3 or more vessels have prominent perivascular cuffs of inflammatory cells with moderate extension of the inflammation into the surrounding parenchyma, and 4=marked the majority of vessels have prominent perivascular cuffs of inflammatory cells with extensive involvement of the neuropil in the inflammatory process.

Total inflammation scores were determined for each of animals for each CNS region.

Mean±SEM (standard error of the mean) score values were computed for each portion of the CNS for each time point and compared against the vehicle treated animals.

The mean inflammatory score were determined for each CNS region for each group of animals and compared statistically against the vehicle control group (students-t-test). These scores are set forth in Tables 8 and 9.

There were no significant histologic alterations in the CNS of animals killed at day 9 post-MBP injection. Lesions at day 14 consisted of minimal to marked mixed (mononuclear+some neutrophils) generally perivascular

TABLE 7

DURATION OF THE DISEASE WITH EVERY THIRD DAY DOSING

| | TNF inhibitor dumbbell mg/kg | | | | |
|---|---|---|---|---|---|
| MBPμg | 0 | 0.1 | 0.3 | 1 | 3 |
| 30 | 5.83 ± 0.44 | 4.83 ± 0.30 | 4.16 ± 0.70 | 3.66 ± 0.61* | 1.83 ± 0.70** |
| 10 | 4.66 ± 0.42 | 5.16 ± 0.40 | 4.00 ± 0.77 | 3.00 ± 0.96 | 2.50 ± 0.67* |
| 3 | 4.00 ± 0.67 | 3.50 ± 0.62 | 3.00 ± 1.35 | 3.00 ± 1.35 | 3.33 ± 0.66 |

*p < 0.05
**p < 0.01

EXAMPLE 18

Central Nervous System (CNS) Pathology

The effects of treatment with c105 dumbbell synthesized using PEG-bis-vinyl sulfone were determined on CNS pathology induced by immunization with MBP (0, 10 or 30 μg). MBP-immunization (EAE induction) was performed as described above. c105 dumbbell at 0.3, 3 mg/kg or vehicle was administered every other day beginning on day nine post MBP. Animals were killed (via $CO_2$) on days 9, 14 or 20 post-MBP injection. The brain and spinal cord from each rat were removed and placed in 10% neutral buffered formalin. Following fixation for at least 72 hours, cross sections of the brain were made at the level of the optic inflammatory cell infiltration. In the brain, the inflammation tended to be located in the meninges, periventricular areas and cerebellar white tracts, with the brain stem and cerebellar white tracts being most severely affected. In these locations, the inflammation often extended from perivascular areas into the surrounding parenchyma and there was evidence of demyelination. Within the spinal cord, the lumbar and sacral portions were most severely affected. Both gray and white matter were affected, again with the predominant lesion being perivascular. Inflammation persisted into day 20, however, neutrophils were rarely seen at this time point. Variability in intensity of inflammation occurred within animals in each group and almost all group.

Tables 8 and 9 demonstrate the presence of c105 dumbbell reduced the degree of inflammation in the various regions of the CNS studied. The most dramatic and significant reductions in inflammation were observed in the spinal cord, particularly the lumbar and sacral regions. c105 dumbbell had a lesser effect on the higher regions of the CNS, cerebrum and cerebellum.

TABLE 8

INFLAMMATORY SCORES OF ANIMALS IMMUNIZED WITH 30 UG MBP AND TREATED WITH TNF INHIBITOR DUMBBELL

| Brain Region | 3 mg/kg | 0.3 mg/kg | Vehicle |
| --- | --- | --- | --- |
| Cerebrum | 1.00 ± 0.378 | 0.714 ± 0.360 | 0.714 ± 0.474 |
| Cerebellum | 2.57 ± 0.429 | 2.714 ± 0.360 | 3.280 ± 0.286 |
| Cervical cord | 1.71 ± 0.360 | 1.428 ± 0.298* | 2.420 ± 0.202 |
| Thoracic cord | 1.71 ± 0.421 | 1.000 ± 0.218* | 2.280 ± 0.421 |
| Lumbar cord | 1.85 ± 0.404 | 1.42 ± 0.369 | 2.42 ± 0.298 |
| Sacral cord | 1.28 ± 0.360 | 1.42 ± 0.298 | 2.714 ± 0.522 |

*$p < 0.05$ (Students t-test)
Histology (30 ug MBP dose)

TABLE 9

INFLAMMATORY SCORES OF ANIMALS IMMUNIZED WITH 10 UG MBP AND TREATED WITH TNF INHIBITOR DUMBBELL

| Brain Region | 3 mg/kg | 0.3 mg/kg | Vehicle |
| --- | --- | --- | --- |
| Cerebrum | 0.28 ± 0.18 | 0.42 ± 0.20 | 0.42 ± 0.29 |
| Cerebellum | 1.42 ± 0.29 | 2.28 ± 0.42 | 2.28 ± 0.35 |
| Cervical cord | 0.85 ± 0.34 | 1.42 ± 0.42 | 1.42 ± 0.20 |
| Thoracic cord | 0.85 ± 0.14 | 1.57 ± 0.36 | 1.0 ± 0.30 |
| Lumbar cord | 0.71 ± 0.28** | 1.57 ± 0.48 | 2.28 ± 0.28 |
| Sacral cord | 0.57 ± 0.20** | 1.57 ± 0.48 | 2.28 ± 0.42 |

**$p < 0.01$
Histology (10 ug MBP dose)

EXAMPLE 19 c105 TNFbp Dumbbell Protects Against Endotoxin Lethality

The c105 dumbbell synthesized using PEG-bis-vinyl sulfone protected Balbic mice against a lethal dose of endotoxin. Mice were injected intraperitoneally with 30 mg/kg endotoxin and intravenously with a single administration of either 0.1 mL PBS or 1 mg/kg dumbbell in 0.1 mL PBS at either 1 hour or two hours after the administration of endotoxin. The intravenous administration of 1 mg/kg dumbbell 1 hour after injection of endotoxin caused almost complete protection against lethality. Dumbbell administration at the two hour time point gave no protection against the lethal endotoxin injury.

The c105 dumbbell also protected Lewis rats against a lethal dose of endotoxin. Rats were injected intravenously with 12.5 mg/kg endotoxin. Rats were injected simultaneously with endotoxin and either saline or the c105 dumbbell at doses of either 0.1, 0.5, 3.0 or 4.5 mg/kg. Comparable protection against lethal injury was achieved at all dumbbell doses.

A single dose treatment of 1.5 mg/kg c105 dumbbell given simultaneously with a 10 mg/kg dose of endotoxin protected rats against hepatic and metabolic disturbances. Hepatic and metabolic parameters were assessed at 24 hours after the administration of endotoxin as shown in Table 10.

TABLE 10

EFFECTS OF TREATMENT WITH c105 DUMBBELL (1.5 MG/KG) ON ENDOTOXIN-INDUCED ABNORMALITIES IN BIOCHEMICAL PARAMETERS

| Parameter | Control + Vehicle | Endotoxin + Vehicle | Endotoxin + c105 dumbbell |
| --- | --- | --- | --- |
| Glucose (mg/dL) | 143 ± 2 | 52 ± 8 | 81 ± 5* |
| SGPT[1] (mu/mL) | 47 ± 6 | 679 ± 118 | 141 ± 25* |
| Blood Urea Nitrogen (mg/dL) | 19 ± 1 | 88 ± 2 | 39 ± 3* |
| Corticosterone (ng/mL) | 164 ± 62 | 750 ± 49 | 489 ± 43* |

[1]Serum Glutamic Pyruvic Transaminase
Values are means ± standard error for 4 to 8 rats per group.
*Significantly different from the endotoxin-treated group at $p < 0.05$ (paired t test)

It is to be understood that the application of the teachings of the present invention to a specific expression system or PEGylation reagent will be within the capabilities of one having ordinary skill in the art in light of the teachings contained herein. Thus, it will be apparent to those of ordinary skill in the art that various modifications and variations can be made in the process and products of the present invention. It is intended that the present invention covers these modifications and variations.

What is claimed is:

1. A compound of the formula $R_1$-X-$R_2$, wherein:
   $R_1$ and $R_2$ are each a tumor necrosis factor (TNF) inhibitor polypeptide selected from:
   (a) 30 kDa TNF inhibitor or 40 kDa TNF inhibitor,
   (b) 30 kDa TNF inhibitor or 40 kDa TNF inhibitor, modified to contain at least one non-native cysteine residue, and
   (c) a biologically active portion of (a) or (b), wherein $R_1$ and $R_2$ bind to TNF; and
   X is a non-peptidic polymer defined as -$Y_1$-$(Z)_n$-$Y_2$-, wherein $Y_1$ and $Y_2$ represent residues of activating groups and $(Z)_n$ represents a base polymeric group wherein $(Z)_n$ is selected from polyethylene glycol, polypropylene glycol, polyoxyethylated glycerol, dextran, colonic acids, poly β-amino acids or carbohydrate polymers.

2. The compound of claim 1 wherein $R_1$ and $R_2$ are identical.

3. The compound of claim 1, wherein $R_1$ and $R_2$ are different.

4. The compound of claim 1, wherein $R_1$ and $R_2$ are said 30 kDa TNF inhibitor.

5. The compound of claim 4, wherein said 30 kDa TNF inhibitor is modified to contain at least one non-native cysteine residue.

6. The compound of claim 5, wherein said non-native cysteine residue is found at an amino acid residue site selected from the group consisting of 1, 14, 105, 111 and 165.

7. The compound of claim 1, wherein $R_1$ and $R_2$ are each a portion of said 30 kDa TNF inhibitor.

8. The compound of claim 1, wherein $R_1$ and $R_2$ are covalently bonded to X by thio-ether bonds.

9. The compound of claim 1, wherein cysteine residues of $R_1$ and $R_2$ are part of said thio-ether bonds.

10. The compound of claim 1, wherein $R_1$ and $R_2$ are attached to said polyethylene glycol via a cysteine residue.

11. A pharmaceutical composition comprised of an effective amount of the compound of claim 1 in a pharmacologically acceptable carrier.

12. The compound of claim 1, which has been prepared by a method comprising simultaneously reacting $R_1$ and $R_2$ with X, wherein X has at least two reactive groups capable of forming thio-ether bonds when reacted with cysteine amino acid residues.

13. The compound of claim 12, wherein $R_1$ and $R_2$ are said 30 kDa TNF inhibitor or a portion thereof, modified to contain a non-native cysteine residue.

14. The compound of claim 12, which has been prepared by a method comprising reacting $R_1$ with X to form a complex $R_1$-X and subsequently reacting said complex $R_1$-X with $R_2$ to form the compound $R_1$-X-$R_2$, wherein X has at least two reactive groups capable of forming thio-ether bonds when reacted with cysteine amino acid residues.

15. The compound of claim 14, wherein $R_1$ and $R_2$ are said 30 kDa TNF inhibitor or a portion thereof, modified to contain a non-native cysteine residue.

* * * * *